(12) United States Patent
Lei et al.

(10) Patent No.: US 9,329,148 B2
(45) Date of Patent: May 3, 2016

(54) HIGH TEMPERATURE SENSOR SELECTIVE FOR PROPANE AND OTHER REDUCING GASES

(71) Applicant: University of Connecticut, Farmington, CT (US)

(72) Inventors: Yu Lei, Mansfield Center, CT (US); Yixin Liu, Ashford, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 14/532,521

(22) Filed: Nov. 4, 2014

(65) Prior Publication Data

US 2015/0123073 A1  May 7, 2015

Related U.S. Application Data

(60) Provisional application No. 61/899,475, filed on Nov. 4, 2013.

(51) Int. Cl.
| | |
|---|---|
| *H01L 29/12* | (2006.01) |
| *G01N 27/12* | (2006.01) |
| *B82Y 15/00* | (2011.01) |
| *G01N 33/00* | (2006.01) |
| *B82Y 30/00* | (2011.01) |

(52) U.S. Cl.
CPC .............. *G01N 27/127* (2013.01); *B82Y 15/00* (2013.01); *G01N 33/004* (2013.01); *G01N 33/0059* (2013.01); *B82Y 30/00* (2013.01); *Y10S 977/955* (2013.01)

(58) Field of Classification Search
CPC ........ H01L 35/08; H01L 35/22; B82Y 15/00; G01N 27/127
USPC ............................................................ 257/43
See application file for complete search history.

(56) References Cited

U.S. PATENT DOCUMENTS

| | | | |
|---|---|---|---|
| 8,211,388 B2 * | 7/2012 | Woodfield et al. ................. 423/1 |
| 2009/0275143 A1 * | 11/2009 | Misra et al. ..................... 436/130 |
| 2011/0227061 A1 * | 9/2011 | Lee et al. ......................... 257/43 |

OTHER PUBLICATIONS

Trovarelli, A. et al., CO2 Methanation Under Transient and Steady-State Conditions over Rh/CeO2 and CeO2-Promoted Rh/SiO2: The Role of Surface and Bulk Ceria, Journal of Catalysis, 151 (1995) pp. 111-124.
Kamiya, M. et al., Intrinsic and Extrinsic Oxygen Diffusion and Surface Exchange Reaction in Cerium Oxide, J. Electrochem. Soc., 147 (2000) pp. 1222-1227.
Savage, N. et al., Composite n-p semiconducting titanium oxides as gas sensors, Sensors and Actuators B-Chemical, 79 (2001) pp. 17-27.
Savage, N.O. et al., Titanium dioxide based high temperature carbon monoxide selective sensor, Sens. Actuator B-Chem., 72 (2001) pp. 239-248.

(Continued)

*Primary Examiner* — David S Blum
(74) *Attorney, Agent, or Firm* — McCarter & English, LLP

(57) ABSTRACT

Exemplary embodiments of the present disclosure relate to sensor technology for gases, and more specifically, to nanofiber based gas sensors capable of operating at high temperatures (e.g., hundreds, thousands of degrees Celsius). In exemplary embodiments, a combination of p-type and n-type nanofiber materials can be combined to create gas sensors that can be used to detect reducing gases with enhanced selectivity/sensitivity.

23 Claims, 18 Drawing Sheets

(56) References Cited

OTHER PUBLICATIONS

Boizumault-Moriceau, P. et al., Oxidative dehydrogenation of propane on Ni—Ce—O oxide: effect of the preparation method, effect of potassium addition and physical characterization, Appl. Catal. A: Gen., 245 (2003) pp. 55-67.

Shan, W.J. et al., Reduction property and catalytic activity of Ce1-XNiXO2 mixed oxide catalysts for CH4 oxidation, Appl. Catal. A: Gen., 246 (2003) pp. 1-9.

Sugiura, M., Oxygen storage materials for automotive catalysts: Ceria-zirconia solid solutions, Catalysis Surveys from Asia, 7 (2003) pp. 77-87.

Xiao, W. et al., Transformation of CeO2(1 1 1) to Ce2O3( 0 0 0 1) films, Chemical Physics Letters, 368 (2003) pp. 527-531.

Campbell, C.T. et al., Oxygen Vacancies and Catalysis on Ceria Surfaces, Science, 309 (2005) pp. 713-714.

Izu, N. et al., Resistive oxygen gas sensors based on Ce1-xZrxO2 nano powder prepared using new precipitation method, Sens. and Actuators B-Chem., 108 (2005) pp. 238-243.

Moos, R., A Brief Overview on Automotive Exhaust Gas Sensors Based on Electroceramics, Int. J. Appl. Ceram. Technol., 2 (2005) pp. 401-413.

Akbar, S. et al., High-Temperature Ceramic Gas Sensors: A review, Int. J. Appl. Ceram. Technol., 3 (2006) pp. 302-311.

Shan, W.J. et al., Syngas production from partial oxidation of methane over Ce1-XNiXOY catalysts prepared by complexation-combustion method, Appl. Catal. A-Gen., 311 (2006) pp. 24-33.

Xu, S. et al., Catalytic performances of NiO—CeO2 for the reforming of methane with CO2 and O2, Fuel, 85 (2006) pp. 2243-2247.

Pakulska, M.M. et al., The effect of metal and support particle size on NiO/CeO2 and NiO/ZrO2 catalyst activity in complete methane oxidation, Applied Catalysis A: General, 332 (2007) pp. 124-129.

Pino, L. et al., Catalytic Performance of Ce1-xNixO2 Catalysts for Propane Oxidative Steam Reforming, Catal. Lett., 122 (2008) pp. 121-130.

Wang, Y. et al., Catalytic reduction of NO by CO over NiO/CeO2 catalyst in stoichiometric NO/CO and NO/CO/O2 reaction, Applied Catalysis B: Environmental, 81 (2008) pp. 141-149.

Sun, J. et al., H-2 production from stable ethanol steam reforming over catalyst of NiO based on flowerlike CeO2 microspheres, Int. J. Hydrog. Energy, 35 (2010) pp. 3087-3091.

Wang, X. et al., Enhanced Oxygen Buffering by Substitutional and Interstitial Ni Point Defects in Ceria: A First-Principles DFT+U Study, Journal of Physical Chemistry C, 114 (2010) pp. 10221-10228.

Huang, H. et al., Low Temperature Growth of SnO2 Nanorod Arrays and Tunable n-p-n Sensing Response of a ZnO/SnO2 Heterojunction for Exclusive Hydrogen Sensors, Advanced Functional Materials, 21 (2011) pp. 2680-2686.

Na, C.W. et al., Selective detection of NO2 and C2H5OH using a Co3O4-decorated ZnO nanowire network sensor, Chemical Communications, 47 (2011) pp. 5148-5150.

Chen, Y.J. et al., Superior ethanol-sensing properties based on Ni-doped SnO2 p-n heterojunction hollow spheres, Sensors and Actuators B: Chemical, 166-167 (2012) pp. 61-67.

Deraz, N.M., Effect of NiO content on structural, surface and catalytic characteristics of nano-crystalline NiO/CeO2 system, Ceram. Int., 38 (2012) pp. 747-753.

Ding, Y. et al., Preparation, characterization and application of novel conductive NiO-CdO nanofibers with dislocation feature, J. Mater. Chem., 22 (2012) pp. 980-986.

Liu, Y.X. et al., CeO2 nanofibers for in situ O-2 and CO sensing in harsh environments, RSC Adv., 2 (2012) pp. 5193-5198.

Liu, Y.X. et al., La0.67Sr0.33MnO3 nanofibers for in situ, real-time, and stable high temperature oxygen sensing, RSC Adv., 2 (2012) pp. 3872-3877.

Solsona, B. et al., Oxidative dehydrogenation of ethane over NiO—CeO2 mixed oxides catalysts, Catal. Today, 180 (2012) pp. 51-58.

Liu, Y. et al., Pt—CeO2 nanofibers based high-frequency impedancemetric gas sensor for selective CO and C3H8 detection in high-temperature harsh environments, Sensors and Actuators B: Chemical, 188 (2013) pp. 1141-1147.

Mahammadunnisa, Sk. et al., NiO/Ce1-xNixO2-delta as an alternative to noble metal catalysts for CO oxidation, Catal. Sci. Technol., 3 (2013) pp. 730-736.

Sun, F.J. et al., Novel Zn—M—O (M=Sn, Co) sensing electrodes for selective mixed potential CO/C3H8 sensors, Sens. Actuator B-Chem., 184 (2013) pp. 220-227.

Liu, Y. et al., Solid-State Gas Sensor for High Temperature Application—A Review, Journal of Material Chemistry, A, (2014).

Liu, Y. et al., Tunable p-n Transition Behaviour of p-La0.67Sr0.33MnO3/n-CeO2 Nanofibers Heterojunction for the Development of Highly Selective Temperature Propane Sensor, Journal of Material Chemistry, A, (2014).

Series 4000 Gas Mixing System, Operating Manual, Revised Mar. 2009, Environics Inc., Tolland, CT, USA.

U.S. Appl. No. 61/899,475, filed Nov. 4, 2013.

* cited by examiner

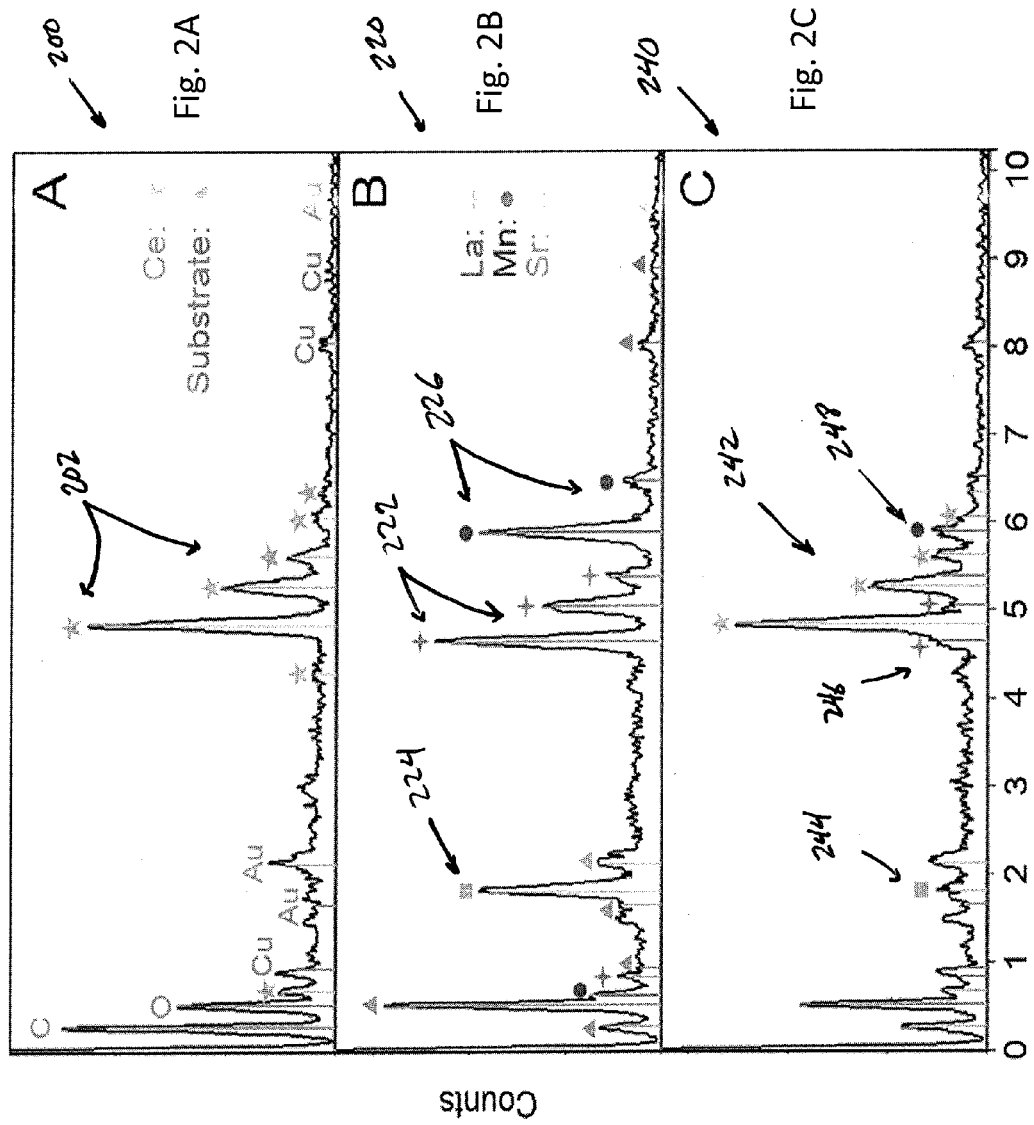

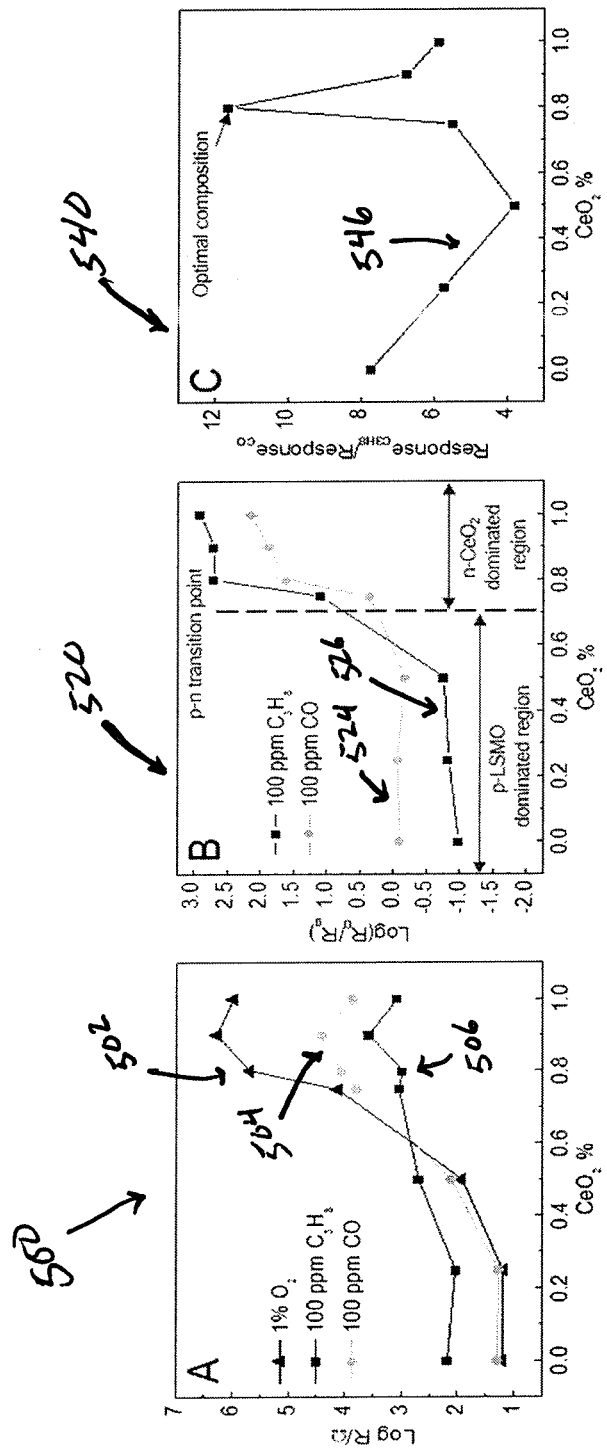

HIGH TEMPERATURE SENSOR SELECTIVE FOR PROPANE AND OTHER REDUCING GASES

CROSS REFERENCE TO RELATED APPLICATIONS

This application claims the benefit of U.S. Provisional Application No. 61/899,475 filed Nov. 4, 2013, the entirety of which is incorporated by reference herein.

FIELD OF TECHNOLOGY

Exemplary embodiments of the disclosure relate to sensor technology for gases, and more specifically, to gas sensors operating at high temperature.

BACKGROUND

The selectivity of a gas sensor is a persistent challenge for most exhausted gas sensors. Currently, potentiometric oxygen sensors based on zirconia are the only reasonably successful commercial high temperature sensors which can work above 800° C. Only limited reports exist on reducing gas detection at high temperature (e.g., approximately 600 to approximately 1200° C.). Other than stability and sensitivity of a sensor at high temperature, selectivity is the most challenging issue. Researchers are trying to fabricate new materials with high selectivity; to design sensing device configurations to include a filter or physical layer; and to use new sensing technology, such as sensor arrays and impedancemetric techniques.

The selectivity of solid-state gas sensors is always challenging for all type of electrochemical sensors, especially to differentiate gases in same group (i.e. reducing gas or oxidizing gas). Researchers have devoted tremendous efforts to improve the sensing selectivity. There are several general strategies. First of all, material design is the most important and fundamental step to endow a sensor with good selectivity. Noble metal/metal oxides and coupled metal oxides are being investigated to achieve good selectivity. In addition, catalytic or physical filter layers are being employed to improve the sensor selectivity, such as Pt catalytic layer and zeolite filter layer. Furthermore, more techniques can be explored to provide more opportunities for enhanced selectivity, such as high-frequency impedancemetric technique and sensor arrays with data analysis. Selectivity becomes more challenging when comes to high temperature above 800° C.

As the most common type of harsh environment sensors, high temperature gas sensors are of paramount importance to improve combustion efficiency and control emissions. Incomplete combustion of fossil fuels, which play a dominant role as a primary energy source for automotive and power industries, leads to the emission of carbon monoxide and hydrocarbon gas. In order to reduce the pollutant emissions and to improve the combustion efficiency, high temperature gas sensors that can provide feedback in real time to combustion processes and monitor emissions are in high demand. There is a current unmet need for such sensors.

On-Board-Diagnostic (OBD) systems usually require gas sensors that can operate in harsh environments at above 500° C. and in close proximity to engines where the exhaust gases can reach temperatures close to 1000° C. To date, commercially available sensor technology for high temperature is extremely limited due to the high requirements for sensing materials and sensor performance in such harsh environments.

Recently, more attention has been given to sensing approaches, such as "impedancemetric" sensing. Impedancemetric sensing employs AC measurements at a specified frequency. This approach is related to solid-state impedance spectroscopy which is an electrochemical characterization technique that measures the cell response over a range of frequencies, typically from subhertz to megahertz. Impedancemetric techniques have been applied on both solid-electrolyte-based sensors and resistor-type sensors. Most of the known impedancemetric sensors operate at low frequency (<100 Hz) because impedance spectra of different concentrations of analyte gas overlap in the high frequency range and the sensors can only get responses at low frequency.

Optimization of a combustion process and evaluation of the exhaust gas after-treatment system are significantly important for energy efficiency improvement and toxic emission reduction, which require control and monitoring of the gas composition. (S. Akbar, P. Dutta, C. H. Lee, High-temperature ceramic gas sensors: A review, *Int. J. Appl. Ceram. Technol.*, 3 (2006) 302-311). These systems usually require measurement of gas concentrations in the high temperature combustion environment, where solid-state electrochemical sensors are particularly suitable. Driven by tighter emission standards, besides already commercialized oxygen sensor, research of $NO_x$ sensors, CO sensors and hydrocarbon sensors is in progress. For direct on-board diagnosis (OBD) purposes, high temperature hydrocarbon sensors employed downstream of a three-way catalytic converter (TWC) can measure the limited components directly, which can provide more precise measurements than dual oxygen sensors (indirectly determining oxygen storage capacity). (R. Moos, A brief overview on automotive exhaust gas sensors based on electroceramics, *Int. J. Appl. Ceram. Technol.*, 2 (2005) 401-413). For this kind of application, the sensor has to withstand hot exhaust gas temperatures that can reach almost 1000° C. and exhaust oxygen contents are almost zero.

It has been reported that p-n heterojunction can be used to improve sensing properties due to the depletion layer at the interface. (C. W. Na, H. S. Woo, I.D. Kim, J. H. Lee, Selective detection of NO2 and C2H5OH using a Co3O4-decorated ZnO nanowire network sensor, *Chemical Communications*, 47 (2011) 5148-5150; Y. J. Chen, L. Yu, D. D. Feng, M. Zhuo, M. Zhang, E. D. Zhang, Z. Xu, Q. H. Li, T. H. Wang, Superior ethanol-sensing properties based on Ni-doped SnO2 p-n heterojunction hollow spheres, *Sensors and Actuators B-Chemical*, 166 (2012) 61-67; H. Huang, H. Gong, C. L. Chow, J. Guo, T. J. White, M. S. Tse, O. K. Tan, Low-Temperature Growth of SnO2 Nanorod Arrays and Tunable n-p-n Sensing Response of a ZnO/SnO2 Heterojunction for Exclusive Hydrogen Sensors, *Advanced Functional Materials*, 21 (2011) 2680-2686). Most of these studies are focused on ZnO and $SnO_2$, and only in low or mild temperature range (<500° C.). Composite n-p titanium oxides have been investigated at high temperature (e.g. approximately 600° C. or greater) to selectively detect CO while eliminating interference from $CH_4$. (N. Savage, B. Chwieroth, A. Ginwalla, B. R. Patton, S. A. Akbar, P. K. Dutta, Composite n-p semiconducting titanium oxides as gas sensors, *Sensors and Actuators B-Chemical*, 79 (2001) 17-27).

SUMMARY

Exemplary embodiments of the present disclosure relate to sensor technology for gases, and more specifically, to nanofiber based gas sensors capable of operating at high temperatures (e.g., hundreds, thousands of degrees Celsius). In exemplary embodiments, a combination of p-type and n-type nanofiber materials can be combined to create gas sensors that can be used to detect reducing gases with enhanced selectivity/sensitivity. For example, exemplary embodiments of the present disclosure provide various compositions of p-type and n-type nanofiber materials to achieve detection of propane with a high sensitivity, while reducing the detection of methane and carbon monoxide to achieve a high selectivity.

In accordance with embodiments of the present disclosure, electrospun LSMO-CeO$_2$ nanofiber composites with different weight ratios (CeO$_2$ wt %:25%, 50%, 70%, 75%, 80% and 90%) can be formed for gas sensors or gas sensor arrays that detect reducing gases. The electrospun LSMO-CeO$_2$ nanofiber composites have a good sensitivity and improved selectivity to C$_3$H$_8$ over CO and CH$_4$ at a high operating temperature (e.g., 600-1200° C.). Enhanced selectivity was seen in experiments using a ratio of L$_{20}$C$_{80}$. Based on p-n heterojunctions with varied ratios, the sensing performance of electrospun LSMO-CeO$_2$ nanofiber composites based sensors can be tuned determine a selectivity and/or sensitivity to reducing gases. In further embodiments disclosed herein, novel nanomaterials and advanced design and fabrication technologies are utilized, by way of example, co-electrospun p-n heterpjunction nanofibers or catalytic/physical filter layers, or combinations thereof.

In accordance with embodiments of the present disclosure, a facile approach to fabricate a sensitive and selective propane sensor based on p-n heterojunctions, which possess good stability and reproducibility at an operating temperature of 800° C. is disclosed. Sensing performance can be optimized by tuning the p/n ratio. The sensing device is simply, easy fabricated and cost-effective. This p-n heterojunction based sensor can minimize the interference from other reducing gases, such as CO and CH$_4$, and selectively detect propane (C$_3$H$_8$).

In accordance with embodiments of the present disclosure, electrospun Ce—Ni—O composite nanofibers can be formed and employed in gas sensors or gas sensor arrays to detect reducing gases (CO, CH$_4$ and C$_3$H$_8$) at high temperature (e.g., 600-1200° C.). Exemplary embodiments of the electrospun Ce—Ni—O composite nanofiber based sensors shows an excellent sensitivity and selectivity towards C$_3$H$_8$. Upon the exposure to reducing gas, highly reactive oxygen species associated with solid solution Ce$_{1-x}$Ni$_x$O$_2$ are firstly consumed, followed by extraction of lattice oxygen in CeO$_2$ and NiO. Due to the different reduction kinetic rates in the first 5 minute (time scale set for sensing), propane can rapidly consume highly reactive oxygen species associated with solid solution Ce$_{1-x}$Ni$_x$O$_2$ and then extract lattice oxygen, leading to significant change of resistance of Ce—Ni—O nanofibers composite, while CO and CH$_4$ possess the sluggish to moderate reduction kinetics, thus only consuming all highly reactive oxygen species. The observed good sensitivity and selectivity can be attributed to such kinetics difference.

In accordance with embodiments of the present disclosure, a facile approach to fabricate sensitive and highly selective propane sensor based on Ce—Ni—O nanofibers is described, in which possess good stability and reproducibility at operating temperatures exceeding 500° C. is achieved. The sensing devices of the present disclosure are simple, easily fabricated, and cost-effective. The good sensitivity and selectivity of the sensor is based on its rapid reaction kinetic with propane. In addition, the responses of n-CeO$_2$ and p-NiO in Ce—Ni—O nanofibers composites towards reducing gas are in opposite direction. Although the offset effect results in an overall reduced sensitivity, the concentration independence of NiO to C$_3$H$_8$ further improves the selectivity of the Ce—Ni—O nanofibers based sensor for propane detection against CO and CH$_4$. Ce—Ni—O nanofibers is a promising material in the development of high temperature gas sensor for selective propane detection.

In accordance with embodiments of the present disclosure, a sensor is disclosed that includes a substrate, one or more electrodes disposed in the substrate, and an electrospun nanofiber composite formed on the substrate. The electrospun nanofiber composite is formed of a p-type nanofiber material and an n-type nanofiber material, wherein the nanofiber composite formed by the p-type nanofiber material and the n-type nanofiber material have selectivity towards detecting a specified type of gas. In some embodiments, the nanofiber composite can have a selectivity towards reducing gases, such as carbon monoxide, methane, and/or propane, and can be operable to detect gas in an environment having a temperature that exceeds at least approximately five hundred degrees Celsius. For example, in some embodiments, the electrospun nanofiber composite can be operable to detect gas in an environment having a temperature between approximately six hundred degrees Celsius and one thousand two-hundred degrees Celsius.

In some embodiments, the p-type material and the n-type material can form one or more p-n junctions.

In some embodiments, the nanofiber composite can be formed from a Lanthanum Strontium Manganate Oxide (LSMO) nanofibers and Cerium (IV) Oxide (CeO$_2$) nanofibers. The LMSO nanofibers can be La$_{0.67}$Sr$_{0.33}$MnO$_3$ nanofibers fabricated by a facile two-step synthetic process that includes electrospinning followed by calcination. The CeO$_2$ nanofibers can fabricated by the facile two-step synthetic process as well.

In some embodiments, the nanofiber composite can have different weight ratios depending on which reducing gases are to be detected by the sensor. In some embodiments, the nanofiber composite can have a weight ratio of approximately eighty percent CeO$_2$ and approximately twenty percent LSMO. In some embodiments, the nanofiber composite has a weight ratio of CeO$_2$ prepared by sonication that is at least one of twenty-five percent, fifty percent, seventy percent, seventy-five percent, eight percent, or ninety percent.

In some embodiments, the sensor comprises an array of gas sensors including a plurality of nanofiber composites including a first nanofiber composite that has a weight ratio of approximately seventy percent CeO$_2$ and approximately thirty percent LSMO and a second nanofiber composite that has a weight ratio of eighty percent CeO$_2$ and approximately twenty percent LSMO. The first nanofiber composite can be operable to distinguish carbon monoxide and propane by opposite response directions. The second nanofiber composite can have a sensitivity and selectivity for propane.

In some embodiments, the nanofiber composite is formed by a metal oxide and Cerium (IV) Oxide (CeO$_2$), where the metal oxide can be Nickel Oxide (NiO).

In some embodiments, the nanofiber composite can have a sensitivity and selectivity for propane such that a response to other reducing gases is mitigated.

In some embodiments, the gas detected by the nanofiber composite corresponds to at least one of carbon monoxide or hydrocarbon gas emitted in an automotive or power industry application.

In accordance with embodiments of the present disclosure a nanofiber composite has a sensitivity and selectivity for detecting a reducing gas. The nanofiber composite includes Lanthanum Strontium Manganate Oxide (LSMO) nanofibers and Cerium (IV) Oxide (CeO$_2$) nanofibers. The LMSO nanofibers and the CeO$_2$ nanofibers are mixed to have a specified weight ratio for sensitivity and selectivity towards a reducing gas. In some embodiments, the nanofiber composite can have a weight ratio of approximately eighty percent $CeO_2$ and approximately twenty percent LSMO. In some embodiments, the nanofiber composite can have a weight ratio of $CeO_2$ prepared by sonication that is at least one of twenty-five percent, fifty percent, seventy percent, seventy-five percent, eight percent, or ninety percent.

In accordance with embodiments of the present disclosure, a nanofiber composite has a sensitivity and selectivity for detecting a reducing gas. The nanofiber composite includes Cerium (IV) Oxide ($CeO_2$) nanofibers and a metal oxide. Nanoparticles formed on a surface of the nanofiber composite comprise the metal oxide and a backbone of the nanofiber composite comprises $CeO_2$ and the metal oxide. In some embodiments, the metal oxide is Nickel Oxide (NiO).

In accordance with embodiments of the present disclosure, an impedancemetric high temperature gas sensor with selectivity towards reducing gas based on electrospun nanofibers is disclosed.

In accordance with embodiments of the present disclosure, a p-$La_{0.67}Sr_{0.33}MnO_3$/n-$CeO_2$ nanofiber heterojunction-based selective high temperature propane sensor is disclosed. As used herein the term "LSMO" refers to Lanthanum Strontium Manganate Oxides and compounds of similar elemental composition.

As disclosed herein a p-n heterojunction based gas sensor can be fabricated for in-situ and real-time detection of propane at high temperature (e.g., 800° C.) with good sensitivity and selectivity. The sensing performance can be optimized by tuning the p/n ratio.

Any combination or permutation of embodiments is envisioned. Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

FIG. 2A depicts an energy-dispersive X-ray spectroscopy analysis of $CeO_2$ nanofibers in accordance with exemplary embodiments of the present disclosure.

FIG. 2B depicts an energy-dispersive X-ray spectroscopy analysis of LSMO nanofibers in accordance with exemplary embodiments of the present disclosure.

FIG. 2C depicts an energy-dispersive X-ray spectroscopy analysis of and $L_{20}C_{80}$ nanofibers composite in accordance with exemplary embodiments of the present disclosure.

FIG. 5A depicts a resistance profile of sensors based on different LSMO-$CeO_2$ weight ratio at 800° C. in 1% $O_2$ and after 5 minutes exposure to one hundred parts per million CO and $C_3H_8$ in accordance with exemplary embodiments of the present disclosure.

FIG. 5B depicts a relation between a response of the sensor towards one hundred parts per million carbon monoxide and one hundred parts per million $C_3H_8$ and $CeO_2$ weight ratio in accordance with exemplary embodiments of the present disclosure.

FIG. 5C depicts a ratio of response (selectivity) to one hundred parts per million $C_3H_8$ over one hundred parts per million CO with increasing $CeO_2$ content in accordance with exemplary embodiments of the present disclosure.

DETAILED DESCRIPTION

Figures 1A, 1B, 1C:
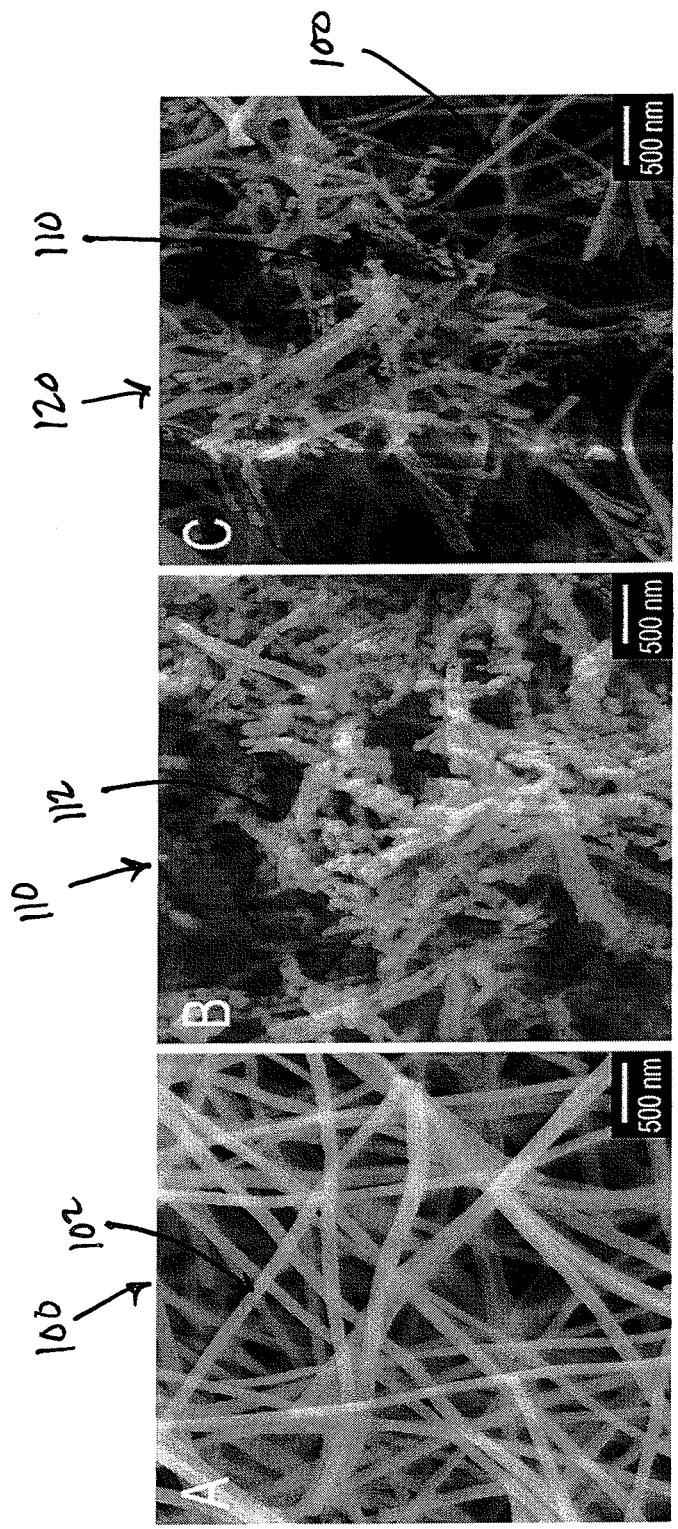
FIG. 1A shows an scanning electron microscopy image of $CeO_2$ nanofibers.
FIG. 1B shows an scanning electron microscopy image of LSMO nanofibers in accordance with exemplary embodiments of the present disclosure.
FIG. 1C shows an scanning electron microscopy image of an $L_{20}C_{80}$ nanofibers composite after sonication in accordance with exemplary embodiments of the present disclosure.

Exemplary embodiments of the present disclosure relate to sensor technology for gases, and more specifically, to nanofiber based gas sensors capable of operating at high temperatures (e.g., hundreds, thousands of degrees Celsius). In exemplary embodiments, a combination of p-type and n-type nanofiber materials can be combined to create gas sensors that can be used to detect reducing gases with enhanced selectivity/sensitivity. For example, exemplary embodiments of the present disclosure provide various compositions of p-type and n-type nanofiber materials to achieve detection of propane with a high sensitivity, while reducing the detection of methane and carbon monoxide to achieve a high selectivity. As described herein, exemplary gas sensors can be formed using a combination of p-type LSMO nanofibers and n-type $CeO_2$ nanofibers, and/or can be formed using Ce—Ni—O composite nanofibers.

As a non-limiting example, exemplary embodiments of the present disclosure provide for electrospun LSMO-$CeO_2$ nanofiber composites with different weight ratio ($CeO_2$ wt %:25%, 50%, 70%, 75%, 80% and 90%) for gas sensors or gas sensor arrays that detect reducing gases. The electrospun LSMO-$CeO_2$ nanofiber composites have a good sensitivity and improved selectivity to $C_3H_8$ over CO and $CH_4$ at a high operating temperature (e.g., 600-1200° C.). Enhanced selectivity was seen in experiments using a ratio of $L_{20}C_{80}$. Based on p-n heterojunctions with varied ratios, the sensing performance of electrospun LSMO-$CeO_2$ nanofiber composites based sensors can be tuned determine a selectivity and/or sensitivity to reducing gases. In further embodiments disclosed herein, novel nanomaterials and advanced design and fabrication technologies are utilized, by way of example, co-electrospun p-n heterpjunction nanofibers or catalytic/physical filter layers, or combinations thereof.

As another non-limiting example, exemplary embodiments of the present disclosure provide for electrospun Ce—Ni—O composite nanofibers to be employed in gas sensors or gas sensor arrays to detect reducing gases (CO, $CH_4$ and $C_3H_8$) at high temperature (e.g., 600-1200° C.). Exemplary embodiments of the electrospun Ce—Ni—O composite nanofiber based sensors shows an excellent sensitivity and selectivity towards $C_3H_8$. Upon the exposure to reducing gas, highly reactive oxygen species associated with solid solution $Ce_{1-x}Ni_xO_2$ are firstly consumed, followed by extraction of lattice oxygen in $CeO_2$ and NiO. Due to the different reduction kinetic rates in the first 5 minute (time scale set for sensing), propane can rapidly consume highly reactive oxygen species associated with solid solution $Ce_{1-x}Ni_xO_2$ and then extract lattice oxygen, leading to significant change of resistance of Ce—Ni—O nanofibers composite, while CO and $CH_4$ possess the sluggish to moderate reduction kinetics, thus only consuming all highly reactive oxygen species. The observed good sensitivity and selectivity can be attributed to such kinetics difference.

I. Combination of P-Type LSMO Nanofibers and N-Type $CeO_2$ Nanofibers for Gas Sensors In the present example, high temperature gas sensors for propane and other reducing gases are formed using a combination of p-type LSMO nanofibers and n-type $CeO_2$ nanofibers, which have been independently shown to have good sensing properties and thermal stability at temperatures of 800° C. and above. For example, LSMO nanofibers have been shown to have good sensing properties and thermal stability at temperatures of 800° C. and above as sert forth in Y. X. Liu, Y. et al., *La0.67Sr0.33MnO3 nanofibers for in situ, real-time, and stable high temperature oxygen sensing*, RSC Adv., 2 (2012) 3872-3877, the entirety of which is incorporated by reference herein. Likewise, $CeO_2$ nanofibers have been shown to have good sensing properties and thermal stability at temperatures of 800° C. and above as set forth in Y. X. Liu, Y. et al., *CeO2 nanofibers for in situ O-2 and CO sensing in harsh environments*, RSC Adv., 2 (2012) 5193-5198, the entirety of which is incorporated by reference herein.

In accordance with exemplary embodiments disclosed herein, p-type LSMO nanofibers and n-type $CeO_2$ nanofibers are combined in different ratios and compositions to identify the p to n transition sensing behavior towards carbon monoxide (CO) and propane ($C_3H_8$). The different ratios and compositions include, for example, ratios and compositions that range from LSMO-dominated mixtures to $CeO_2$-dominated mixtures. Select ratios and compositions for the combined p-type LSMO nanofibers and n-type $CeO_2$ nanofibers gas sensors (combination-based sensors) were employed in in-situ and real-time detection of reducing gases (e.g., CO, $CH_4$ and $C_3H_8$) at high temperature (e.g., 800° C.).

Experimental Data

The preparation procedures of LSMO ($La_x$—$Sr_y$—Mn oxide) and $CeO_2$ nanofibers are similar to that in previous reports. (Y. X. Liu, Y. Ding, H. Y. Gao, L. C. Zhang, P. X. Gao, B. K. Li, Y. Lei, La0.67Sr0.33MnO3 nanofibers for in situ, real-time, and stable high temperature oxygen sensing, *RSC Adv.*, 2 (2012) 3872-3877; Y. X. Liu, Y. Ding, L. C. Zhang, P. X. Gao, Y. Lei, CeO2 nanofibers for in situ O-2 and CO sensing in harsh environments, *RSC Adv.*, 2 (2012) 5193-5198). Briefly, and as a non-limiting example, the LSMO nanofibers can be formed by dissolving a total weight of 0.386 grams of metal salts (the molar ratio of La$(NO_3)_3.6H_2O$, $Sr(NO_3)_3$ and $Mn(NO_3)_2.4H_2O$ is 0.67:0.33:1) in 3 milliliters (mL) Dimethylformamide (DMF) and 0.2 mL water, after which 0.386 grams of Polyvinylpyrrolidone (PVP) can be added. After stirring overnight, the final homogeneous precursor solution can be loaded into a plastic syringe with a 19-gauge needle for electrospinning. The $La(NO_3)_3$—$Sr(NO_3)_2$—$Mn(NO_3)_3$-PVP nanofibers can be generated by electrospinning with a flow rate of 0.3 mL/hour at an applied voltage of 20 kilovolts (kV) over a collection distance of 15 centimeters (cm). Similarly, and as a non-limiting example, the $CeO_2$ nanofibers can be formed by dissolving 0.386 grams of $Ce(NO_3)_3.6H_2O$ and 0.386 g PVP in 3 mL DMF to fabricate the $Ce(NO_3)_3$-PVP precursor nanofibers by electrospinning with the same parameters as the LSMO nanofibers. Both of the as-prepared precursor nanofibers can be subjected to a two-stage calcination process. Using this calcination process, in a first stage, the samples are calcined at 500° C. for 3 hours to remove the matrix polymer and generate LSMO and $CeO_2$ nanofibers; and in a second stage, the samples are calcined at 800° C. for another 3 hours to improve the crystal structure and thermal stability of these metal oxides nanofibers.

A series of LSMO-$CeO_2$ nanofiber mixtures with different weight ratios ($CeO_2$ wt %: 25%, 50%, 70%, 75%, 80%, 90%) were prepared by a physical method of sonication. Due to the extreme light weight of LSMO and $CeO_2$ nanofiber, pure LSMO nanofiber and $CeO_2$ nanofiber suspensions can be first prepared by suspending the nanofibers in ethanol at the same concentration of 10 mg/ml, in order to precisely control both the ratio of the two components and the total loading. Both of the single component suspensions can be sonicated in a water bath for 30 minutes. Subsequently, the LSMO-$CeO_2$ nanofiber mixture suspension with different weight ratios can be controlled by a volume ratio using a pipette. As a non-limiting example, a total volume of the mixture suspension for sensor fabrication can be fixed at approximately 200 µl. The mixture suspensions can be sonicated for another 30 minutes to ensure uniform mixing.

A series of resistor-type LSMO-$CeO_2$ nanofiber composite-based sensors can be fabricated on a suitable substrate. As a non-limiting example, the composite-based sensors can be experimentally formed on $Al_2O_3$ ceramic screws (4-40×½") (e.g., an $Al_2O_3$ ceramic substrate). Before fabrication of a sensor on the ceramic substrate, the ceramic substrate, can be sonicated in $HNO_3$ (1M) and ethanol successively to remove the contaminants on the surface. After dried, the ceramic substrate in the form of the $Al_2O_3$ ceramic screw, for example, can be tightly tied by two platinum (Pt) wires on two close threads, serving as two electrodes. The as-prepared 200 µl LSMO-$CeO_2$ nanofiber composite suspension (2 µg nanofiber composites) can be cast onto the substrate to bridge the two Pt electrodes. 200 µl of single component LSMO and $CeO_2$ nanofiber suspension were also prepared for sensor fabrication as a control experiment. Sensor devices based on LSMO-$CeO_2$ nanofiber composite with different ratios ($CeO_2$ wt %: 25%, 50%, 70%, 75%, 80%, and 90%) were experimentally formed and denoted as $L_{75}C_{25}$, $L_{50}C_{50}$, $L_{30}C_{70}$, $L_{25}C_{75}$, $L_{20}C_{80}$ and $L_{10}C_{90}$. The sensor was connected to a CHI 601C electrochemical analyzer (CH Instruments Inc., USA) through two long Ni—Cr alloy wires and was placed in the centre of a furnace with a temperature control to conduct in-situ high temperature gas sensing. The current output at a fixed 1 V DC bias was continuously measured.

The performance of the LSMO-$CeO_2$ nanofiber composite-based gas sensors at high temperature of 800° C. were evaluated by measuring the resistance/conductance change upon exposure to different concentrations of reducing gas (CO, $CH_4$ and $C_3H_8$) in a dynamic gas flow system. At 800° C., reducing gases will react with $O_2$, therefore, high purity nitrogen was used as the carrying gas instead of air, and 1% $O_2$ was used as recovering gas. The sensor was subjected to a gas flow with a constant flow rate of 1.5 L/min, which were regulated by a computer-controlled gas mixing system (S-4000, Environics Inc., USA). The current in the sensor was continuously measured and the electric resistance of the sensor was calculated by applying Ohm's Law (R=V/I). In a typical reducing gas sensing experiment, CO for example, the sensor placed in a furnace at 800° C. was first exposed to a $CO/N_2$ mixture for 5 minutes, followed by exposure to 1% $O_2$ for 10 minutes to recover the sensor, and then the "exposure/recovery" cycle was repeated. In order to compare the sensitivity of an as-fabricated series of sensors, which included p-type LSMO dominated sensors and n-type $CeO_2$ dominated sensors, different sensitivity definitions were used in this study. Upon the exposure to reducing gas, the resistance of the p-type sensors increases, so the sensitivity was defined as $R_g/R_0$ to keep the number larger than 1, where $R_0$ is the initial electrical resistance of the sensor in 1% $O_2$ and $R_g$ is the measured real-time resistance upon exposure to reducing gas/nitrogen mixture or 1% $O_2$ recovering gas. On the contrary, the resistance of n-type sensor decreases when reducing gas presents, where the sensitivity was defined as $R_0/R_g$ (>1). For overall evaluation of sensor performance, $log(R_0/R_g)$ was used.

Since all the sensors were fabricated based on a suspension of nanofibers after sonication, the morphologies of sonicated LSMO nanofibers, $CeO_2$ nanofibers and one representative LSMO-$CeO_2$ nanofiber composite ($L_{20}C_{80}$, optimal composition from gas sensing experiments) were first examined by scanning electron microscopy (SEM). FIGS. 1A-C show SEM images of $CeO_2$ nanofibers, LSMO nanofibers, and an $L_{20}C_{80}$ nanofiber composite after sonication. As shown in FIG. 1A, $CeO_2$ nanofibers 100 are shown after two-step calcination, in which PVP matrix was completely degraded and $Ce(NO_3)_3$ was decomposed to form $CeO_2$, displayed uniform and well-distributed fiber structure 102 with an average diameter of 109±17 nm. The surfaces are smooth indicating the good morphological thermal stability. After sonication, $CeO_2$ nanofibers were broken down to small pieces with the size about several μm, instead of individual short nanofibers aggregate. The $CeO_2$ fibers still kept their morphology with a relatively long length. On the contrary, as shown in FIG. 1B, LSMO nanofibers 110 showed rougher surface than $CeO_2$ nanofibers with an average diameter of 117±15 nm. Although LSMO nanofibers still retrained the nanofibrous structure 112, large grains and pores can be observed, providing large surface area. One can also notice that sonicated LSMO nanofibers posessed a shorter length around 1-2 μm. After mixing $CeO_2$ and LSMO nanofibers together, shown in FIG. 1C, the mixture 120 exhibited a hybrid morphology with the combination of both types of nanofibers (i.e. $CeO_2$ nanofibers 100 and LSMO nanofibers 110). For a $L_{20}C_{80}$ nanofiber composite, which is dominated by $CeO_2$, the majority was long $CeO_2$ fiber pieces, as a matrix, and the LSMO short fibers were dispersed into and bridged the $CeO_2$ nanofibers.

Energy-dispersive X-ray spectroscopy (EDX) can be employed to investigative the composition of LSMO nanofibers, $CeO_2$ nanofibers, and the $L_{20}C_{80}$ nanofiber composite. FIGS. 2A-C show an EDX analysis of $CeO_2$ nanofibers, LSMO nanofibers and the $L_{20}C_{80}$ nanofiber composite. As shown in FIGS. 2A and 2B, the EDX spectra 200 and 220, respectively clearly indicate the presence of Ce (denoted by stars 202) in $CeO_2$ nanofibers and La (denoted by plus signs 222), Sr (denoted by squares 224), Mn (denoted by circles 226) elements in LSMO nanofibers. The carbon peak, Cu peak and Au peak shown in FIGS. 2A-C can be attributed to the carbon tape, copper tape and Au sputtering coation using in SEM samples preparation. Compare the EDX spectrum of $L_{20}C_{80}$ nanofiber composite (FIG. 2C) to FIG. 1, the major peaks 242 have good agreement with the peaks of $CeO_2$, indicating that $CeO_2$ was the dominating component. The new peak 244 near 1.8 eV, the shoulder peak 246 at 4.6 eV and the new peak 248 at 5.9 eV, corresponding to Sr, La and Mn, respectively, revealed the presence of LSMO in the mixture.

Figure 3:
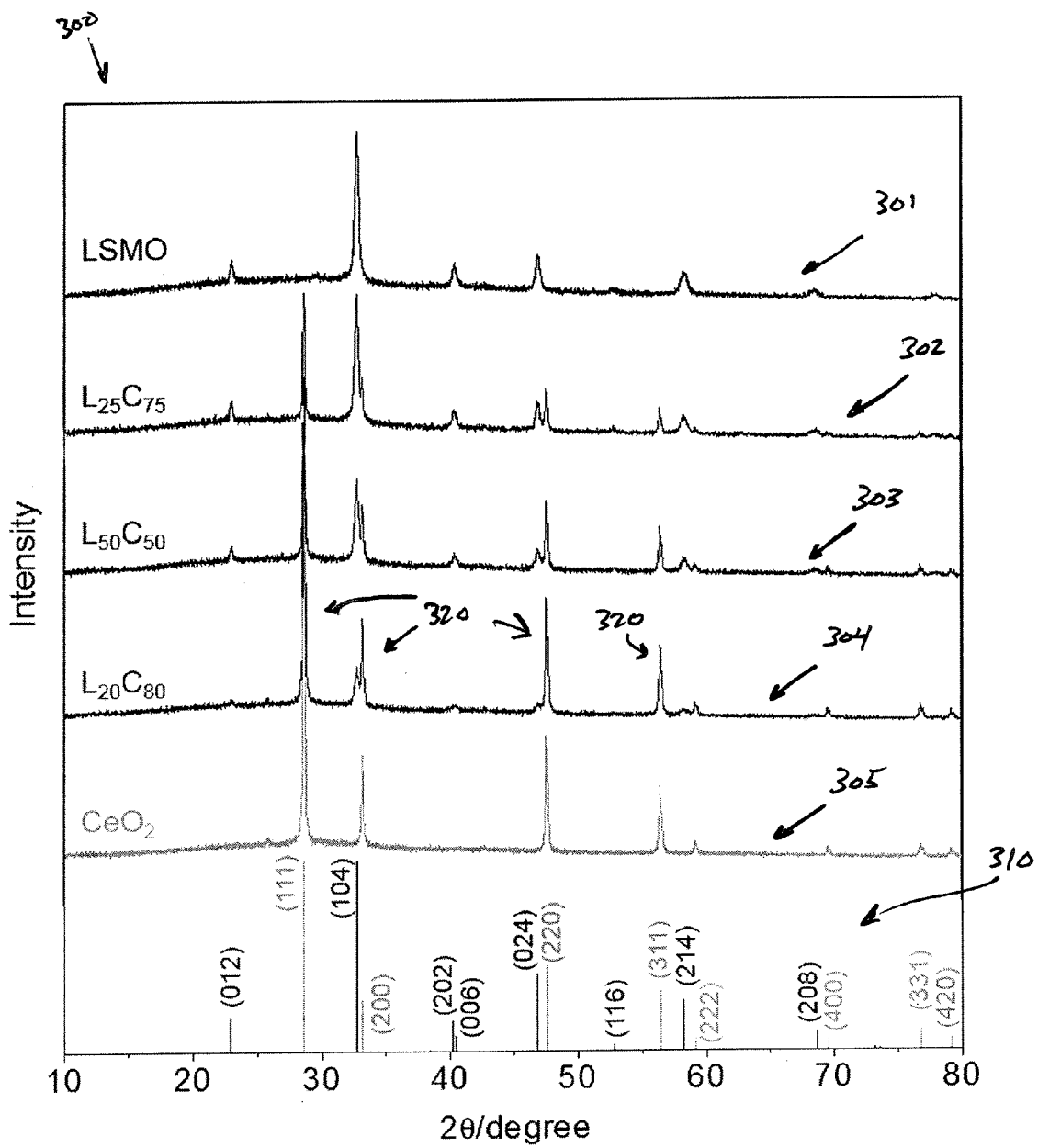
FIG. 3 depicts X-ray diffraction patterns for the LSMO, $L_{25}C_{75}$, $L_{50}C_{50}$, $L_{20}C_{80}$ and $CeO_2$ nanofibers and standard values for $CeO_2$ and $La_{0.65}Sr_{0.35}MnO_3$ in accordance with exemplary embodiments of the present disclosure.

FIG. 3 depicts a graph 300 that shows X-ray diffraction (XRD) patterns 301-305 that characterize the composition and crystal structures of LSMO, $L_{25}C_{75}$, $L50C_{50}$, $L_{20}C_{80}$ and $CeO_2$ nanofibers, respectively, and shows standard values 310 for $CeO_2$ and $La_{0.65}Sr_{0.35}MnO_3$. The major peaks 320 in XRD pattern of the $L_{20}C_{80}$ nanofiber composite matches the standard $CeO_2$ spectrum of JCPDS 65-5923. The diffraction peaks at 2θ values of 28.59, 33.13, 47.56, 56.43, 59.18, 69.53, 76.83, 79.21° correspond to $CeO_2$ (111), (200), (220), (311), (222), (400), (331) and (420) crystal planes, respectively. According to the standard spectrum of LSMO (JCPDS 54-1195), the diffraction peaks appear at 2θ values of 22.91, 32.70, 40.18, 40.47, 46.92, 52.83, 58.16, 68.58° corresponding to (012), (104), (202), (006), (024), (116), (214) and (208) crystal planes, respectively. Due to the low weight ratio of LSMO in the mixture, the peaks of LSMO were weak. However, an obvious shoulder peak at 32.70, which is the strongest diffraction peak of LSMO clearly indicate the presence of LSMO crystallite.

Figures 4A, 4B:
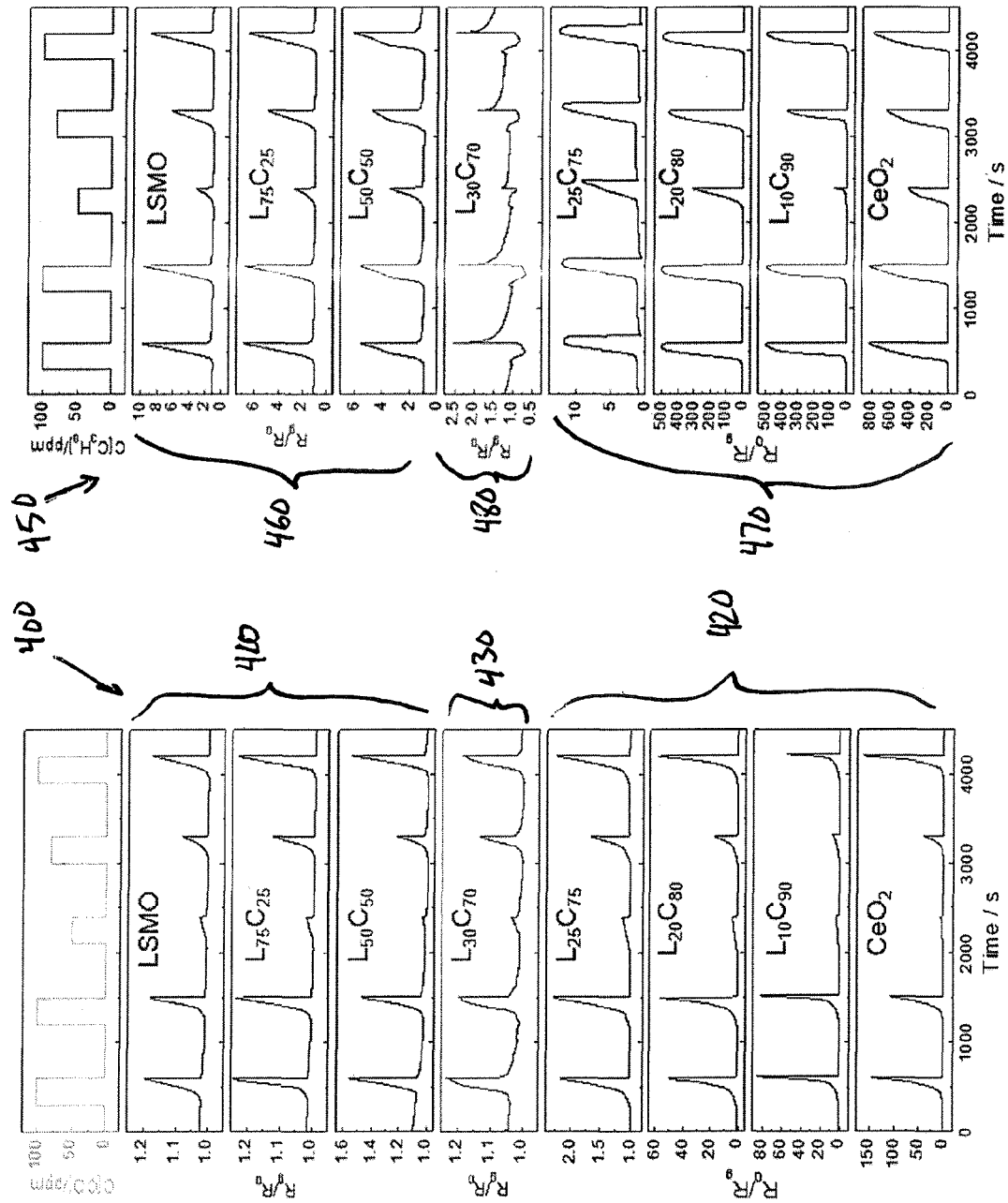
FIG. 4A depicts responses of a series of sensors as a function of time upon periodic exposure to different concentrations of carbon monoxide in accordance with exemplary embodiments of the present disclosure.
FIG. 4B depicts responses of a series of sensors as a function of time upon periodic exposure to different concentrations of $C_3H_8$ in accordance with exemplary embodiments of the present disclosure.

A series of sensors based on LSMO-$CeO_2$ nanofiber composites with different weight ratio were tested at high temperature of 800° C., and pure LSMO and $CeO_2$ nanofibers were studied as control. Based on the I-V characteristics of these sensors at 800° C. in 1% $O_2$, all sensors obey Ohm's Law, indicated by I-V straight line (not shown). All sensors were employed to detect CO and $C_3H_8$ balanced by $N_2$ with the concentration of 50, 80 and one hundred parts per million (100 ppm) at 800° C. FIGS. 4A-B present graphs 400 and 450 showing responses of the series of sensors as a function of time upon periodic exposure to different concentrations of carbon monoxide (CO) (as shown in the graphs 400) and propane ($C_3H_8$) (as shown in the graphs 450). The sensor responses of LSMO-$CeO_2$ nanofiber composite-based sensors are based upon periodic exposure to different concentrations of carbon monoxide (FIG. 4A) and propane (FIG. 4B) at an applied DC bias of 1 V at 800° C. (For $L_{20}C_{80}$, $L_{10}C_{90}$ and $CeO_2$, the reverse resistance ratio $R_0/R_g$ initiated from 1, which cannot be shown in figure due to the scale.)

As presented in FIGS. 4A-B, all the sensors with varied compositions, except the transition point $L_{30}C_{70}$, showed fast response, rapid recovery, and concentration dependent behavior to both carbon monoxide (CO) and propane ($C_3H_8$). In addition, good reproducibility of these sensors can be shown by the same level response to the same concentration of reducing gas (first two and last one cycles are in same concentration). For example, with respect to the $L_{20}C_{80}$ compositions, which provides excellent sensitive and selective propane detection, a calculated RSD of sensor responses towards three-time exposure to 100 ppm CO and 100 ppm $C_3H_8$ are 8.0% and 0.2%, respectively, which indicates excellent reproducibility of propane detection.

FIG. 5A depicts a graph 500 that shows resistance profile of sensors based on different LSMO-$CeO_2$ weight ratio at 800° C. in 1% $O_2$ (denoted by line 502) and after 5 minutes exposure to 100 ppm CO (denoted by line 504) and $C_3H_8$ (denoted by line 506). FIG. 5B depicts a graph 520 that shows a relation between the response of the sensor towards 100 ppm CO (denoted by line 524) and 100 ppm $C_3H_8$ (denoted by line 526), and $CeO_2$ weight ratio. FIG. 5C depicts a graph 540 that shows the ratio of response (selectivity) to 100 ppm $C_3H_8$ (denoted by line 546) over 100 ppm CO with increasing $CeO_2$ content.

The resistance of each sensor (e.g., sensor formed by compositions of $L_{75}C_{25}$, $L_{50}C_{50}$, $L_{30}C_{70}$, $L_{25}C_{75}$, $L_{20}C_{80}$ and $L_{10}C_{90}$) in 1% $O_2$ and after 5 minutes exposure to 100 ppm CO and 100 ppm $C_3H_8$ are summarized in the graph 500 shown in FIG. 5A. LSMO is a p-type semiconductor and very conductive at high temperature, whose half-metallicity has been reported to be associated with $Mn^{3+}$ valency, while $CeO_2$ is an n-type semiconductor and has a large resistance about one mega-ohm (MS2) at 800° C. From the reducing gas detection results shown in FIGS. 4A-B, it can be determined that with increasing $CeO_2$ content, the $L_{30}C_{70}$ composite corresponds to the transition composition from LSMO dominated p-type composite to $CeO_2$ dominated n-type composite.

With reference to FIG. 5A, in the LSMO dominated region ($CeO_2$ wt %<70%), with increasing $CeO_2$ content, the resistance gradually increased, but still relatively conductive (resistance within kilo-ohms (kΩ)). It is possible that the short LSMO nanofibers aggregated as a matrix, and small $CeO_2$ nanofibers pieces were isolated in the mixture. With increasing $CeO_2$ content, the resistance increased because the holes in LSMO were trapped by electrons in $CeO_2$ forming a p-n heterojunction and because of the large resistance of $CeO_2$. In the $CeO_2$ dominated region ($CeO_2$ wt %>70%), with increasing LSMO content, the resistance first increased ($L_{10}C_{90}$), which can be ascribe to the formation of local depletion layer in $CeO_2$ induced by small amount of LSMO nanofibers in the mixture. With further increasing LSMO content, the resistance of the mixture decreased again due to the high conductivity of LSMO.

As mentioned above, $L_{30}C_{70}$ was the p-n transition composition. When the $CeO_2$ content was smaller than 70%, the sensors showed overall p-type sensing behavior, therefore, $R_g/R_0$ was used to evaluate the sensing performance. Upon the exposure of p-type sensors to reducing gas, the resistance $R_g$ and response ratio $R_g/R_0$ increased, as shown in graphs 410 and 460 in FIGS. 4A-B, respectively. With increasing $CeO_2$ content, the sensitivity of the sensors towards CO almost remained at the same level, while the sensitivity towards $C_3H_8$ gradually decreased, resulting in the less selectivity to $C_3H_8$ over CO, as summarized in graphs 520 and 540 of FIGS. 5B and 5C, respectively. When the $CeO_2$ content further increased beyond 70%, the sensors transformed from p-type to n-type composite, showing overall n-type sensing behavior, where the reversed resistance ratio of $R_0/R_g$ was employed. As shown in graphs 420 and 470 in FIGS. 4A-B, respectively, upon the exposure of n-type sensors to reducing gas, the resistance $R_g$ decreased 2~3 decades dramatically, leading to the reversed ratio $R_0/R_g$ jumping up to several hundred for propane detection. With the increasing addition of LSMO, the response of n-$CeO_2$ dominated sensor towards CO decreased proportionally to the LSMO content. Although the response towards $C_3H_8$ also slightly decreased, the sensitivity to $C_3H_8$ still maintained at a very high level, providing enhanced selectivity to $C_3H_8$ over CO from pure $CeO_2$ to $L_{20}C_{80}$, as shown in the graph 540 of FIG. 5C.

Based on the comprehensive sensing profiles of LSMO-$CeO_2$ nanofibers with varied compositions as shown in FIGS. 4A-B, the transformation of the sensor behavior from p-type to n-type in response to increasing $CeO_2$ content can be seen. Notably, at the p-n transition point, the sensor $L_{30}C_{70}$ showed opposite direction responses to CO and $C_3H_8$, as presented in the graphs 430 and 480 of FIGS. 4A-B, respectively. For $L_{30}C_{70}$, the sensor still showed p-type behavior towards CO, which is similar to other p-LSMO dominated sensors. However, upon the exposure to $C_3H_8$, the resistance decreased, showing n-type sensing behavior. When the recovering gas of 1% $O_2$ was supplied, the resistance increased immediately and then gradually decreased to a plateau instead of a stable straight line. These results further provided the sensing profile near p-n transition point, which may contribute to an understanding of sensing mechanisms.

Figure 6:
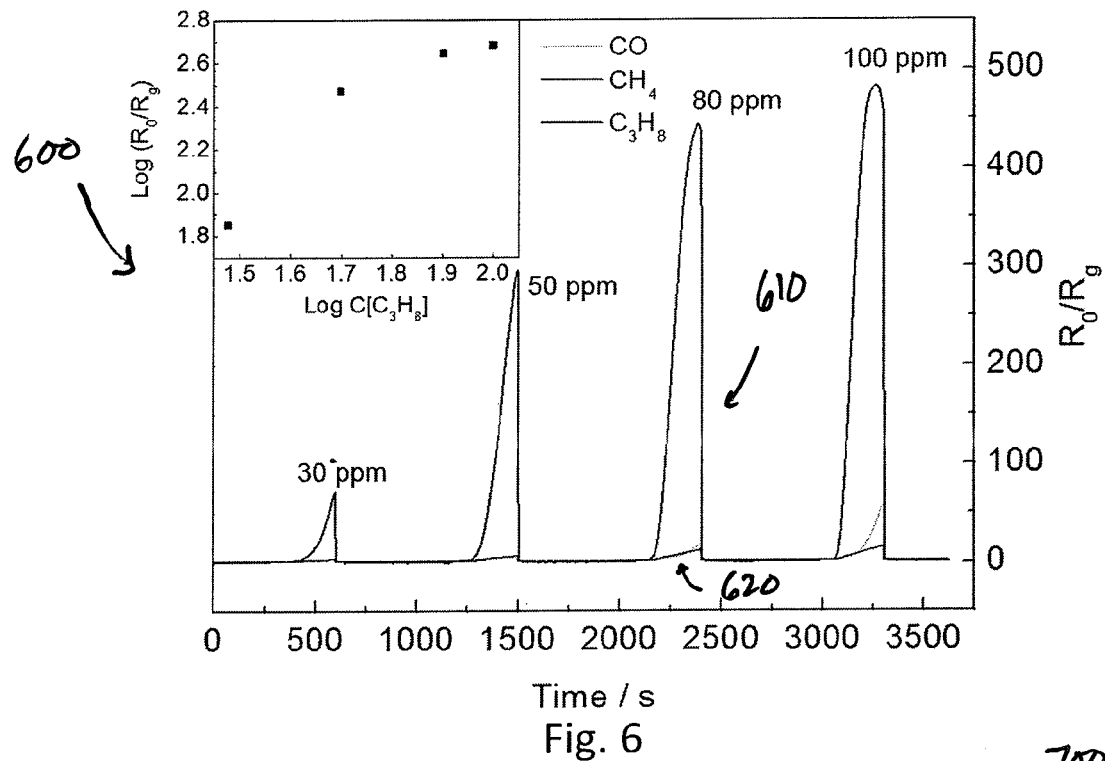
FIG. 6 depicts sensor responses of $L_{20}C_{80}$ nanofibers composite-based sensor upon periodic exposure to different concentrations of carbon monoxide, methane and propane at an applied DC bias of one volt at 800° C. in accordance with exemplary embodiments of the present disclosure.

As shown herein, the $L_{20}C_{80}$ composition appear to be most suitable for propane ($C_3H_8$) detection due to its enhanced selectivity and good sensitivity. Experiments with the $L_{20}C_{80}$ composition were carried out to further investigate its ability to detect CO, $CH_4$ and $C_3H_8$ at 800° C. FIG. 6 is a graph 600 that shows a response of a $L_{20}C_{80}$ nanofiber composite-based sensor upon periodic exposure to different concentrations of carbon monoxide, methane and propane at an applied DC bias of 1 V at 800° C. As shown by the curve 610 in FIG. 6, the $L_{20}C_{80}$ composite-based sensor showed fast, reversible and concentration dependent response to CO, $CH_4$ and $C_3H_8$. The line 620 is a calibration curve for propane. The sensor exhibits ultra-sensitivity to $C_3H_8$ and only limited response to CO and $CH_4$. Based on the calibration curve presented in the inset, the sensing response towards $C_3H_8$ tends to reach saturation at high concentrations up to 100 ppm, because the number of oxygen vacancies which can form in $CeO_2$ is limited. High concentrations of $C_3H_8$ consume almost all oxygen which can be extracted, transforming $CeO_2$ to $Ce_2O_3$.

Figure 7:
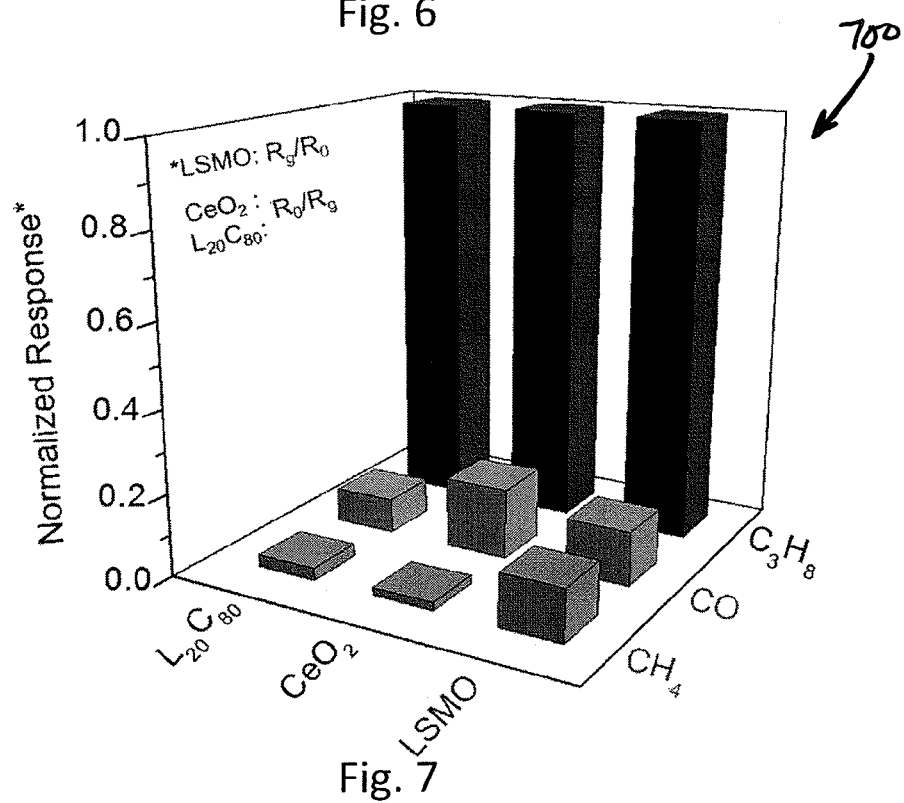
FIG. 7 depicts sensitivity/selectivity of the LSMO nanofibers, $CeO_2$ nanofibers and optimal $L_{20}C_{80}$ nanofibers composite-based sensor towards reducing gas (CO, $CH_4$ and $C_3H_8$) at 800° C. in accordance with exemplary embodiments of the present disclosure.

FIG. 7 is a graph 700 that summarizes sensitivity/selectivity of the LSMO nanofiber, $CeO_2$ nanofiber and the $L_{20}C_{80}$ nanofiber composite-based sensors towards reducing gas (CO, $CH_4$ and $C_3H_8$) at 800° C. Based on the in-situ gas detection results, the $L_{20}C_{80}$ nanofiber composite based sensor showed improved selectivity to $C_3H_8$ over CO and $CH_4$ compared to pure LSMO nanofibers and $CeO_2$ nanofibers. A normalized response was used to evaluate the selectivity among $L_{20}C_{80}$, $CeO_2$ and LSMO, using the response towards 100 ppm $C_3H_8$ as response value of 1. As compared in FIG. 7, 100 ppm CO introduced 16.8% and 13.0% interference to the response of $CeO_2$ and LSMO towards 100 ppm $C_3H_8$, respectively, and only 8.3% to the response of $L_{20}C_{80}$ towards 100 ppm $C_3H_8$. Similarly, 100 ppm $CH_4$ introduced 12.7% interference to the response of LSMO towards 100 ppm $C_3H_8$, while only 2.0% and 3.0% to that of $CeO_2$ and $L_{20}C_{80}$, respectively. As-prepared $L_{20}C_{80}$ p-n heterojunction-based sensor showed fast, sensitive, reversible, and reproducible response towards $C_3H_8$ with improved selectivity, suggesting that $L_{20}C_{80}$ is a good sensing material in the detection of $C_3H_8$ in high temperature harsh environment.

As disclosed herein $La_{0.67}Sr_{0.33}MnO_3$ nanofibers and $CeO_2$ nanofibers were successfully fabricated by a facile two-step synthetic route (electrospinning followed by calcination). The LSMO-$CeO_2$ nanofiber composites were prepared by sonication with different weight ratio ($CeO_2$ wt %:25%, 50%, 70%, 75%, 80% and 90%). The series of sensors based on LSMO-$CeO_2$ nanofiber composites clearly showed p-n transition behavior from p-LSMO dominated composite to n-$CeO_2$ dominated composite. At the p-n transition composition ($L_{30}C_{70}$), the sensor exhibited p-type characteristics for CO detection, while it exhibited n-type sensing behaviour to $C_3H_8$. $L_{20}C_{80}$ was a preferred composition, which showed good sensitivity and improved selectivity to $C_3H_8$ over CO and $CH_4$ at a high operating temperature of 800° C. The enhanced selectivity of $L_{20}C_{80}$ and the opposite response of $L_{30}C_{70}$ to CO and $C_3H_8$ are ascribed to the change of depletion layer thickness.

Based on p-n heterojunctions with varied ratios, the sensing performance of sensors designed and fabricated as disclosed herein can be tuned. Combined with the $L_{30}C_{70}$-like material, which can distinguish CO and propane by opposite response direction, and $L_{20}C_{80}$-like material with good sensitivity and selectivity, sensor arrays can be designed for highly selective gas detection.

II. Ce—Ni—O Composite Nanofibers for Gas Sensors

Cerium (IV) oxide ($CeO_2$) with cubic fluorite structure has long been considered as one of the most important rare-earth oxide materials for applications in the fields of energy and environment, including heterogeneous catalysts, solid oxide fuel cells (SOFCs) and solid-state gas sensors. Beside its desirable properties such as good transmission, excellent adhesion and high stability against mechanical abrasion, chemical attack and high temperature (W. Xiao, Q. Guo, E. G. Wang, Transformation of CeO2(1 1 1) to Ce2O3(0 0 0 1) films, *Chemical Physics Letters,* 368 (2003) 527-531), $CeO_2$ has attracted increasing attention in recent years due to its high oxygen storage capability (OSC). (M. Sugiura, Oxygen storage materials for automotive catalysts: Ceria-zirconia solid solutions, *Catalysis Surveys from Asia,* 7 (2003) 77-87; C. T. Campbell, C. H. F. Peden, Oxygen vacancies and catalysis on ceria surfaces, *Science,* 309 (2005) 713-714). Lattice oxygen in cerium oxide can be rapidly released and reversibly formed without decomposing, leading to a free transformation among non-stoichiometric compositions ($CeO_{2-x}$) with two limiting cases ($CeO_2$ and $Ce_2O_3$). Due to this capacity, $CeO_2$-based catalysts have been extensively investigated in the past, in which $CeO_2$ takes an active catalytic role in several chemical reactions, such as purification of exhaust gases, hydrogen production via the water-gas shift reaction, or selective CO oxidation. It was reported that the promoting effect of ceria is attributed to the generation and participation of surface oxygen species and anionic vacancies in the catalytic reactions. (A. Trovarelli, C. Deleitenburg, G. Dolcetti, J. L. Lorca, CO2 Methanation Under Transient and Steady-State Conditions over Rh/CeO2 and CeO2-Promoted Rh/SiO2: The Role of Surface and Bulk Ceria, *Journal of Catalysis,* 151 (1995) 111-124).

Benefiting from the high oxygen storage capability, good thermal stability and large diffusion coefficient of oxygen vacancy, CeO$_2$ has also been employed as sensing material for harsh environment gas detection, especially at high temperature up to 1000° C. (M. Kamiya, E. Shimada, Y. Ikuma, M. Komatsu, H. Haneda, Intrinsic and extrinsic oxygen diffusion and surface exchange reaction in cerium oxide, *J. Electrochem. Soc.*, 147 (2000) 1222-1227; N. Izu, N. Oh-hori, M. Itou, W. Shin, I. Matsubara, N. Murayama, Resistive oxygen gas sensors based on Ce1-xZrxO2 nano powder prepared using new precipitation method, *Sens. Actuator B-Chem.*, 108 (2005) 238-243; Y. X. Liu, Y. Ding, L. C. Zhang, P. X. Gao, Y. Lei, CeO2 nanofibers for in situ O-2 and CO sensing in harsh environments, Rsc Advances, 2 (2012) 5193-5198). Ceria has an insulator-like behaviour in the stoichiometric oxidized state CeO$_2$ and becomes conductive in the reduced state CeO$_{2-x}$, that is assisted by the reduction of Ce$^{4+}$ ions to Ce$^{3+}$ following electron localization into Ce 4f states. By measuring the resistance change of sensing material (e.g., CeO$_2$) and establishing the relation between resistance of the sensor and the concentration of target gas, the sensor can be employed to predict the analyte concentration. High temperature gas sensors, which are of paramount importance for combustion process control and toxic emission monitoring in a wide range of industries, usually require the sensors being operated at high temperature with good sensitivity, selectivity and long-term stability. (Y. Liu, J. Parisi, X. Sun, Y. Lei, Solid-State Gas Sensor for High Temperature Application—A Review, *Journal of Material Chemistry, A*, (2014)). Beside the conventional high temperature oxygen sensors, high temperature CO and hydrocarbon sensors are also considered as necessary to directly determine the fuel combustion efficiency and catalytic efficiency of three-way catalytic converters for direct on-board diagnosis (OBD) purposes. In our previous study (Y. X. Liu, Y. Ding, L. C. Zhang, P. X. Gao, Y. Lei, CeO2 nanofibers for in situ O-2 and CO sensing in harsh environments, *Rsc Advances*, 2 (2012) 5193-5198), electrospun CeO$_2$ nanofibers-based resistive sensor exhibited excellent sensitivity to reducing gas (CO) and an opposite response to O$_2$ with good recoverability, reproducibility and thermal stability at high operating temperature of 800° C. In order to eliminate responses from oxidizing gases, Pt doped CeO$_2$ nanofibers was recently investigated for selective detection of reducing gases with the assistance of high frequency impedancemetric sensing technique. (Y. Liu, Y. Lei, Pt—CeO$_2$ nanofibers based high-frequency impedancemetric gas sensor for selective CO and C3H8 detection in high-temperature harsh environment, *Sensors and Actuators B: Chemical*, 188 (2013) 1141-1147). Enhanced sensitivity of the sensor towards CO was also observed with the addition of Pt into CeO$_2$, which is contributed by the strong catalytic activity of Pt. Among all challenges encountered by high temperature gas sensors, selectivity remains the most prominent one for all types of sensors despite of the fact that tremendous efforts have been made to solve this problem in past three decades. A fundamental approach to improve the selectivity of the high temperature gas sensors is to design and develop novel sensing materials endowing the sensor with intrinsic selectivity towards the specific target gas. In this regard, metal oxides composites are popularly employed to tune the selectivity of gas sensors. Many hybrid systems have been reported such as anatase/La$_2$O$_3$/CuO composite (N. O. Savage, S. A. Akbar, P. K. Dutta, Titanium dioxide based high temperature carbon monoxide selective sensor, *Sens. Actuator B-Chem.*, 72 (2001) 239-248) and anatase-rutile (n-p) composite (N. Savage, B. Chwieroth, A. Ginwalla, B. R. Patton, S. A. Akbar, P. K. Dutta, Composite n-p semiconducting titanium oxides as gas sensors, *Sens. Actuator B-Chem.*, 79 (2001) 17-27) for selective CO detection against CH$_4$, Zn—Sn—O composite with preference to CO than C$_3$H$_8$, and ZnCo$_2$O$_4$ with selectivity to C$_3$H$_8$ over CO (F. J. Sun, X. G. Li, L. P. Liu, J. Wang, Novel Zn-M-O (M=Sn, Co) sensing electrodes for selective mixed potential CO/C3H8 sensors, *Sens. Actuator B-Chem.*, 184 (2013) 220-227).

In accordance with exemplary embodiments of the present disclosure, the metal oxide NiO was incorporated into CeO$_2$ to form gas sensors for selective propane detection, taking advantages of demonstrated overall excellent sensing properties of CeO$_2$ towards propane. Many studies have shown that the reducibility and catalytic activity of CeO$_2$ can be considerably enhanced by doping with small amounts of transition metals. (X. Wang, M. Shen, J. Wang, S. Fabris, Enhanced oxygen buffering by substitutional and interstitial Ni point defects in ceria: A first-principles DFT+U study, *Journal of Physical Chemistry C*, 114 (2010) 10221-10228). Particularly, CeO$_2$—NiO catalysts have been studied in many catalytic reactions, including CO oxidation (S. Mahammadunnisa, P. M. K. Reddy, N. Lingaiah, C. Subrahmanyam, NiO/Ce1-xNixO2-delta as an alternative to noble metal catalysts for CO oxidation, *Catal. Sci. Technol.*, 3 (2013) 730-736), NO reduction (Y. Wang, A. Zhu, Y. Zhang, C. T. Au, X. Yang, C. Shi, Catalytic reduction of NO by CO over NiO/CeO2 catalyst in stoichiometric NO/CO and NO/CO/O2 reaction, *Applied Catalysis B: Environmental*, 81 (2008) 141-149), methane combustion (M. M. Pakulska, C. M. Grgicak, J. B. Giorgi, The effect of metal and support particle size on NiO/CeO2 and NiO/ZrO2 catalyst activity in complete methane oxidation, *Applied Catalysis A: General*, 332 (2007) 124-129), methane reforming with CO$_2$ and O$_2$ (S. Xu, X. Yan, X. Wang, Catalytic performances of NiO—CeO2 for the reforming of methane with CO2 and O2, Fuel, 85 (2006) 2243-2247), ethanol/propane steam reforming (J. Sun, Y. G. Wang, J. G. Li, G. L. Xiao, L. G. Zhang, H. Li, Y. L. Cheng, C. W. Sun, Z. X. Cheng, Z. C. Dong, L. Q. Chen, H-2 production from stable ethanol steam reforming over catalyst of NiO based on flowerlike CeO2 microspheres, *Int. J. Hydrog. Energy*, 35 (2010) 3087-3091; L. Pino, A. Vita, F. Cipiti, M. Lagana, V. Recupero, Catalytic performance of Ce1-xNixO2 catalysts for propane oxidative steam reforming, *Catal. Lett.*, 122 (2008) 121-130), and ethanol/propane dehydrogenation (P. Boizumault-Moriceau, A. Pennequin, B. Grzybowska, Y. Barbaux, Oxidative dehydrogenation of propane on Ni—Ce—O oxide: effect of the preparation method, effect of potassium addition and physical characterization, *Appl. Catal. A-Gen.*, 245 (2003) 55-67; B. Solsona, P. Concepcion, S. Hernandez, B. Demicol, J. M. L. Nieto, Oxidative dehydrogenation of ethane over NiO—CeO2 mixed oxides catalysts, *Catal. Today*, 180 (2012) 51-58). The synergistic effect of NiO and CeO$_2$ with enhanced O buffering effect of ceria by Ni-doping is thought to be crucial for the high catalytic activities in these reactions.

Experimental Data

As described herein, Ce—Ni—O composite nanofibers were successfully prepared by electrospinning and a subsequent calcination process. The morphology of as-prepared composite nanofibers was characterized by scanning electron microscopy (SEM) and transmission electron microscopy (TEM). The composition and crystal structure of Ce—Ni—O nanofibers were investigated in detail by energy dispersive X-ray analysis (EDX), X-ray diffraction (XRD), EDX line scanning, element mapping and high resolution-TEM (HR-TEM). The gas sensing performance of composite nanofibers based sensor towards CO, CH$_4$ and C$_3$H$_8$ was investigate at 800° C. The sensing mechanism of the enhanced selectivity for C$_3$H$_8$ was proposed. This study opens an avenue in the design of high temperature gas sensor with high performance.

To prepare Ce—Ni—O nanofibers, the total weight of 0.386 g metal salts (the molar ratio of Ce(NO$_3$)$_3$.6H$_2$O and Ni(NO$_3$)$_2$.6H$_2$O is 1:1) were dissolved in 3 mL DMF and then 0.386 g PVP was added. After stirring overnight, the final homogeneous precursory solution was loaded into a plastic syringe with a 19-gauge needle for electrospinning. The Ce(NO$_3$)$_3$—Ni(NO$_3$)$_2$-PVP nanofibers were generated by electrospinning with a flow rate of 0.3 mL/h at an applied voltage of 20 kV over a collection distance of 15 cm. The as-prepared precursor nanofibers were then subjected to a two-stage calcination process. First, the sample was calcined at 500° C. for 3 h to remove the matrix polymer and generate Ce—Ni—O nanofibers; and then calcined at 800° C. for another 3 h to improve the crystal structure and thermal stability of the metal oxides nanofibers. NiO nanofibers were prepared in a similar way using Ni(NO$_3$)$_2$.6H$_2$O-PVP-DMF as a precursor solution.

A resistor-type Ce—Ni—O nanofiber composite-based sensors were fabricated on Al$_2$O$_3$ ceramic screws (4-40×½"), as reported previously. (Y. Liu, Y. Lei, Pt—CeO2 nanofibers based high-frequency impedancemetric gas sensor for selective CO and C3H8 detection in high-temperature harsh environment, *Sensors and Actuators B: Chemical*, 188 (2013) 1141-1147). Before fabrication, the ceramic screw, acting as substrate, was sonicated in HNO$_3$ (1M) and ethanol successively to remove the contaminants on the surface. After drying, it was tightly tied by two Pt wires on two close threads, serving as two electrodes. Ce—Ni—O nanofibers suspensions were first prepared by suspending the nanofibers in ethanol at a concentration of 10 mg/mL followed by sonication in water bath for 30 min. 200 µL of as-prepared Ce—Ni—O nanofiber suspension (total 2 µg nanofibers) was centrifuged and then casted onto the substrate and bridged the two Pt electrodes to complete the sensor fabrication. The sensor was connected to a CHI 660C electrochemical analyzer (CH Instruments Inc., USA) through two long Ni—Cr alloy wires and was placed in the centre of a furnace with a temperature control to conduct in-situ high temperature gas sensing. The current output at a fixed 1 V DC bias was continuously measured.

The performance of Ce—Ni—O nanofiber composite-based gas sensors and two control sensors (CeO$_2$ nanofibers and NiO nanofibers-based) at high temperature of 800° C. were evaluated by measuring the resistance/conductance change upon exposure to different concentrations of reducing gas (CO, CH$_4$ and C$_3$H$_8$) in a dynamic gas flow system. At 800° C., reducing gases could react with O$_2$, therefore, high purity nitrogen was used as the carrying gas of various reducing gases instead of air, and 1% O$_2$ (in N$_2$) was used as the sensor-recovering gas. The sensor was subjected to a gas flow with a constant flow rate of 1.5 L/min, which were regulated by a computer-controlled gas mixing system (S-4000, Environics Inc., USA). The current in the sensor was continuously measured and the electric resistance of the sensor was calculated by applying Ohm's Law (R=V/I). In a typical reducing gas sensing experiment, C$_3$H$_8$ for example, the sensor placed in furnace at 800° C. was first exposed to C$_3$H$_8$/N$_2$ mixture for 5 min, followed by 1% O$_2$ for 10 min to recover the sensor, and then the "exposure/recovery" cycle was repeated. Upon the exposure to reducing gas, the resistance of the n-type sensors (Ce—Ni—O nanofibers and CeO$_2$ nanofibers as a control) increases, so the sensitivity was defined as R$_0$/R$_g$ to keep the number larger than 1, where R$_0$ is the initial electrical resistance of the sensor in 1% O$_2$ and R$_g$ is the measured real-time resistance upon exposure to reducing gas/nitrogen mixture or 1% O$_2$ recovering gas. NiO nanofibers were also investigated as the other control, which exhibited p-type sensing behavior, using R$_g$/R$_0$ as sensitivity for better comparison.

Figure 8A:
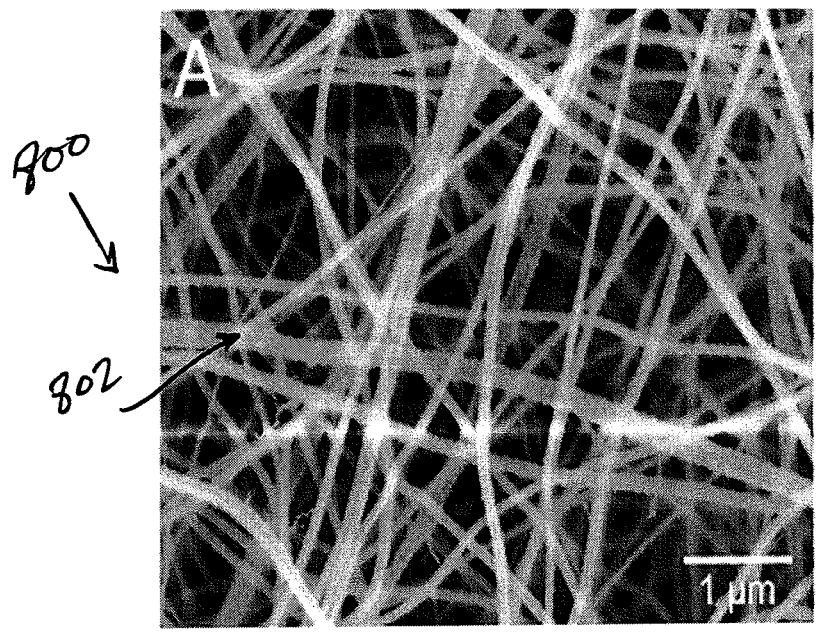
FIG. 8A depicts a scanning electron microscopy image of Ce—Ni—O nanofibers in low magnification in accordance with exemplary embodiments of the present disclosure.
Figure 8B:
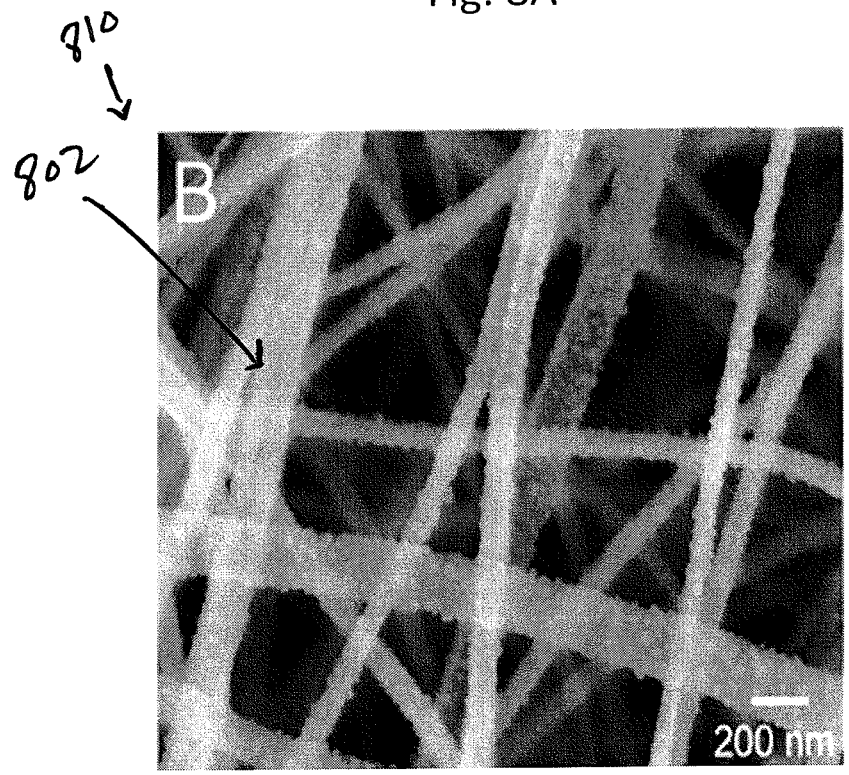
FIG. 8B depicts a scanning electron microscopy image of Ce—Ni—O nanofibers in high magnification in accordance with exemplary embodiments of the present disclosure.
Figure 8C:
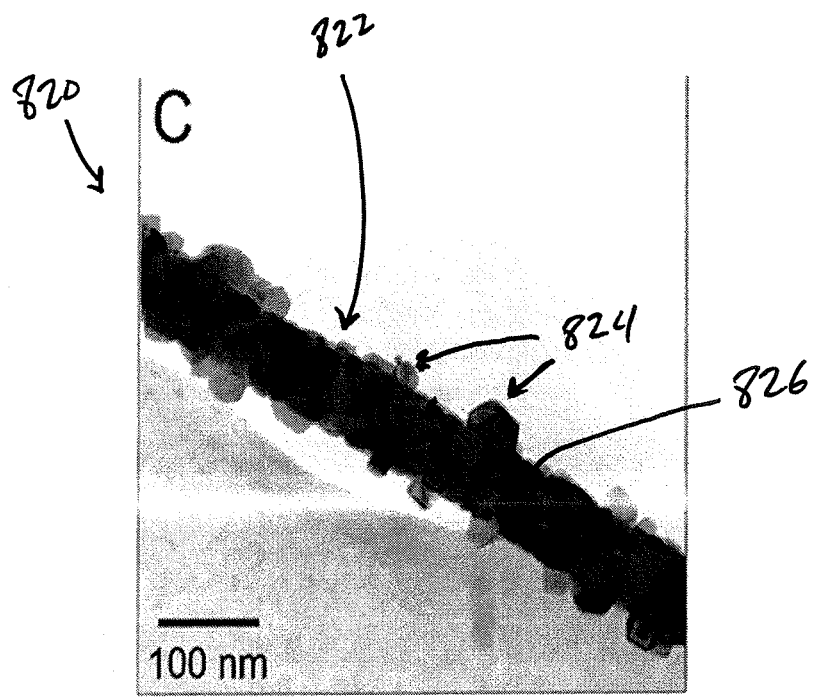
FIG. 8C depicts a transmission electron microscopy image of a single Ce—Ni—O nanofiber in accordance with exemplary embodiments of the present disclosure.
Figure 8D:
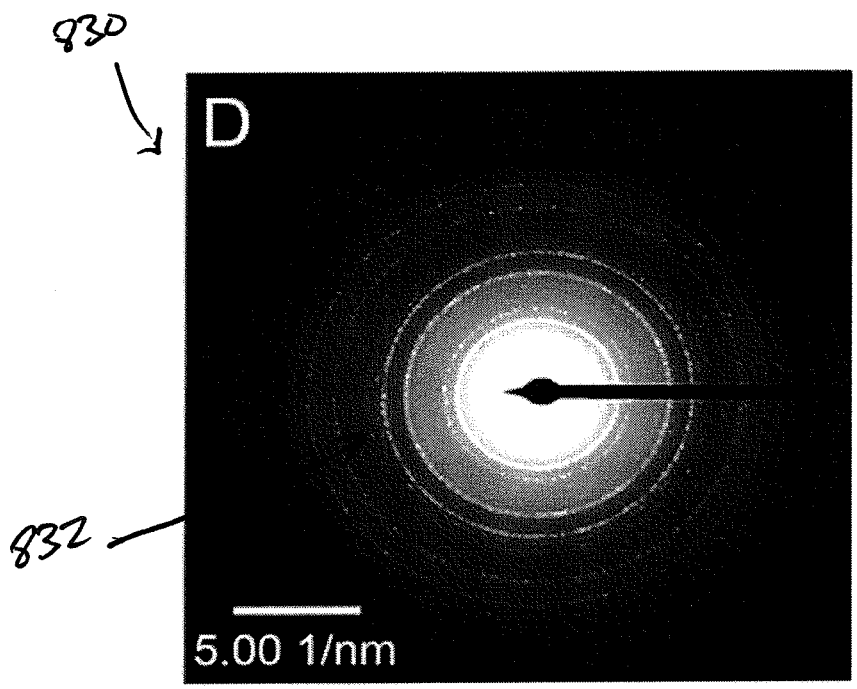
FIG. 8D depicts a selected area (electron) diffraction pattern of the Ce—Ni—O nanofibers in accordance with exemplary embodiments of the present disclosure.

FIG. 8A shows an SEM image 800 of Ce—Ni—O nanofibers 802 in low magnification. FIG. 8B shows an SEM image 810 of Ce—Ni—O nanofibers 802 in high magnification. FIG. 8C shows a TEM image 820 of a single Ce—Ni—O nanofiber 822. FIG. 8D shows an image 830 of a SAED pattern 832 of the Ce—Ni—O nanofibers. SEM is employed to investigate the morphology of the Ce—Ni—O nanofibers after two-step calcination, as shown in FIGS. 8A-B. From FIG. 8A, which is in low magnification, it can be seen that the as-prepared Ce—Ni—O nanofibers 802 have an overall uniform distribution with a small average diameter of 89±10 nm, except that a very few nanobelts were observed with a larger width of around 176 nm. The formation of nanobelts may be attributed to the incomplete drying of the electrospun fibers before reaching the collector. (Y. Ding, Y. Wang, L. C. Zhang, H. Zhang, Y. Lei, Preparation, characterization and application of novel conductive NiO—CdO nanofibers with dislocation feature, *J. Mater. Chem.*, 22 (2012) 980-986). When zoom in the SEM image to a higher magnification, FIG. 8B shows numerous small nanoparticles are well-distributed on the surface of Ce—Ni—O nanofibers. To further investigate the morphology of Ce—Ni—O nanofibers, TEM was carried out, as shown in FIG. 8C. The TEM image 820 of the individual Ce—Ni—O nanofiber 822 is decorated with a number of nanoparticles 824 on the surface 826 of the nanofiber 822, which is in a good agreement with SEM results. The nanofiber backbone possesses a diameter of ~80 nm and the nanoparticles 824 on the surface 826 shows a wider size distribution with a proximately average diameter of 25±7 nm. In addition, small grains can be observed. The selected area electron diffraction (SAED) image 830 of FIG. 8D shows a typical ring pattern that indicates that the nanofibers 802 have a polycrystalline structure.

Figure 9A:
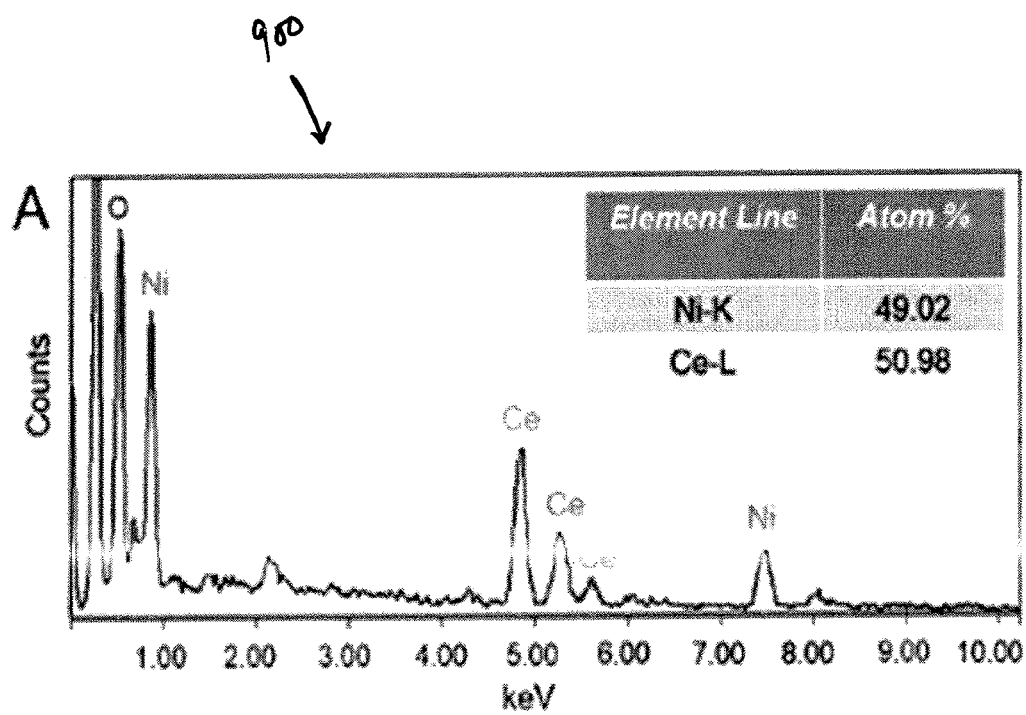
FIG. 9A depicts an energy-dispersive X-ray spectroscopy analysis of Ce—Ni—O nanofibers in accordance with exemplary embodiments of the present disclosure.
Figure 9B:
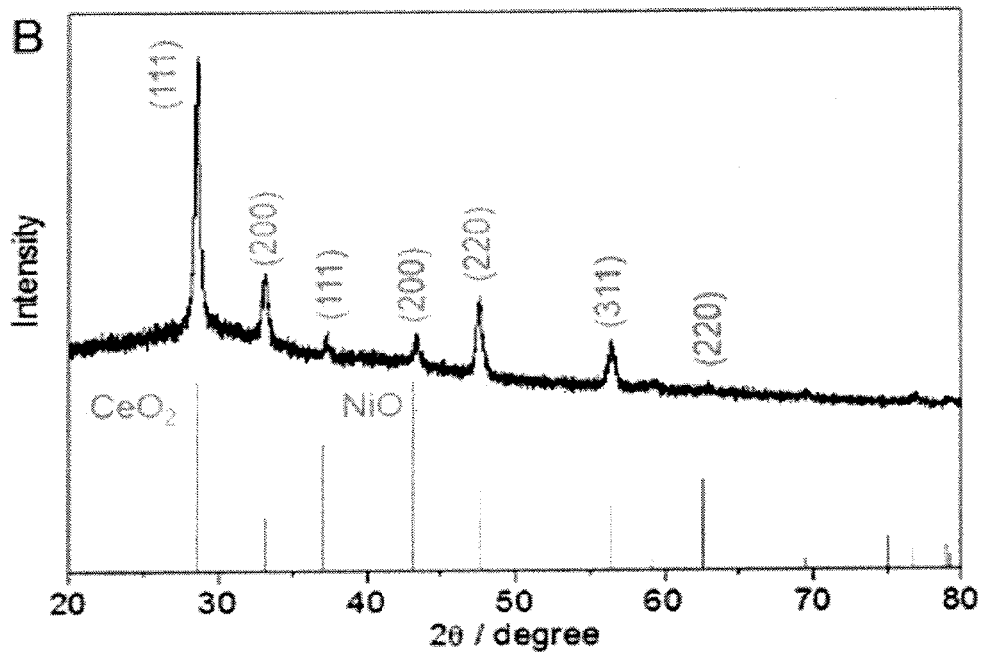
FIG. 9B depicts X-ray diffraction patterns for Ce—Ni—O nanofibers and standard values for $CeO_2$ and NiO in accordance with exemplary embodiments of the present disclosure.

The overall composition and crystal structure of Ce—Ni—O nanofibers can first be characterized by EDX and XRD. FIG. 9A depicts a graph 900 showing an EDX analysis of Ce—Ni—O nanofibers. FIG. 9B depicts a graph 920 showing XRD patterns for the Ce—Ni—O nanofibers and the standard values for CeO$_2$ (orange lines) and NiO (green lines). The presence of Ce and Ni elements in Ce—Ni—O is revealed by the EDX spectrum with a closed equal atom percentage, as presented in FIG. 9A and its inset, which affirms the formation of Ce—Ni—O. The XRD pattern of Ce—Ni—O nanofiber matches the combined standard spectrum of CeO$_2$ (JCPDS 65-5923) and NiO (JCPDS 65-2901), as shown in FIG. 9B, indicating the separate phase of CeO$_2$ and NiO. The formation of CeO$_2$ is revealed by the diffraction peaks at 2θ values of 28.59, 33.13, 47.56, 56.43, 59.18, 69.53, 76.83, 79.21° corresponding to (111), (200), (220), (311), (222), (400), (331) and (420) crystal planes of CeO$_2$, respectively, while the diffraction peaks at 2θ values of 37.09, 43.10, 62.58, 75.04 and 79.00° correspond to (111), (200), (220), (311) and (222) crystal planes of cubic crystalline NiO, respectively.

Figure 10A:
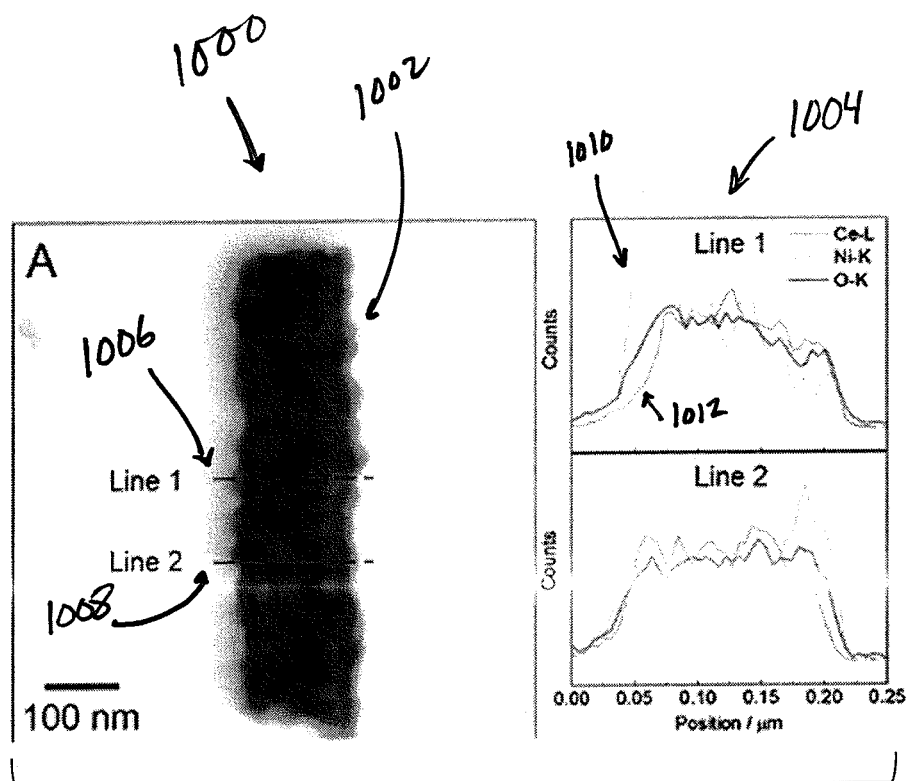
FIG. 10A shows a scanning transmission electron microscopy image of a single Ce—Ni—O nanofiber and energy-dispersive X-ray spectroscopy line scanning spectra of Ce, Ni and O elements in accordance with exemplary embodiments of the present disclosure.
Figure 10B:
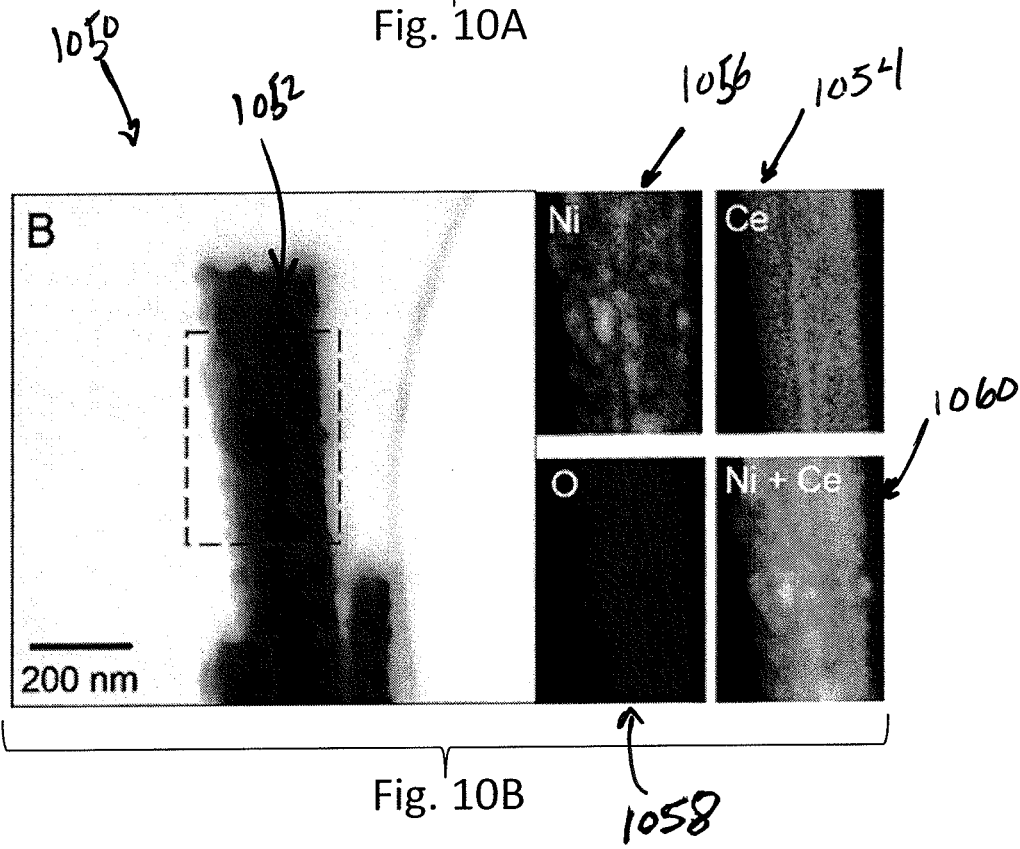
FIG. 10B shows a scanning transmission electron microscopy image of a Ce—Ni—O nanobelt and energy-dispersive X-ray spectroscopy mapping of Ce, Ni and O elements in accordance with exemplary embodiments of the present disclosure.

The detailed composition and crystal structure within single Ce—Ni—O nanofibers was further investigated by Scanning TEM. FIG. 10A depicts a Scanning TEM image 1000 of a single Ce—Ni—O nanofiber 1002 and EDX line scanning spectra 1004 of Ce, Ni and O elements. FIG. 10B depicts a Scanning TEM image 1050 of a Ce—Ni—O nanobelt 1052 and EDX mappings 1054, 1056, 1058, and 1060 of Ce, Ni, O, and Ni+Ce elements, respectively. As shown in FIG. 10A, the EDX line scanning spectra 1004 corresponds to two lines 1006 and 1008. For both of line scanning spectra, the intensity of O is maintained at a relatively stable level and the intensity of Ce and Ni fluctuates around the O spectrum in opposite direction, which further validates the separate phase of $CeO_2$ and NiO. In addition, from the spectrum of line 1006, it can be seen that the intensity 1010 of Ni near the left edge is exceptional high while very limited Ce counts (intensity 1012 of Ce) are detected at the same position, indicating the nanoparticle on the nanofiber surface could be mainly NiO. Similar phenomenon can also be observed in the spectrum of line 1008 near the right edge. Moreover, in both spectra, Ni possesses a wider position range of element intensity and high intensity near the edge than Ce, suggesting that NiO could be the rich phase near the Ce—Ni—O nanofiber surface. The same conclusion can be drawn from EDX mapping, which provides a more comprehensive profile for element distribution. As shown in FIG. 10B, EDX mapping is conducted on the Ce—Ni—O nanobelt 1052, whose large width is beneficial for better image considering the resolution of scanning TEM and EDX detector. The distributions of Ce and O are relatively homogenous along the nanobelt 1052. Although Ni is also well-distributed in the whole nanofiber 1052, an obvious grain-based pattern can be seen in the mapping image. By incorporating the Ni and Ce element maps in the same image, a sheer green shell, corresponding to Ni, can be observed, which further affirms the previous conclusion that NiO is preferential on the surface of Ce—Ni—O.

Figure 11A:
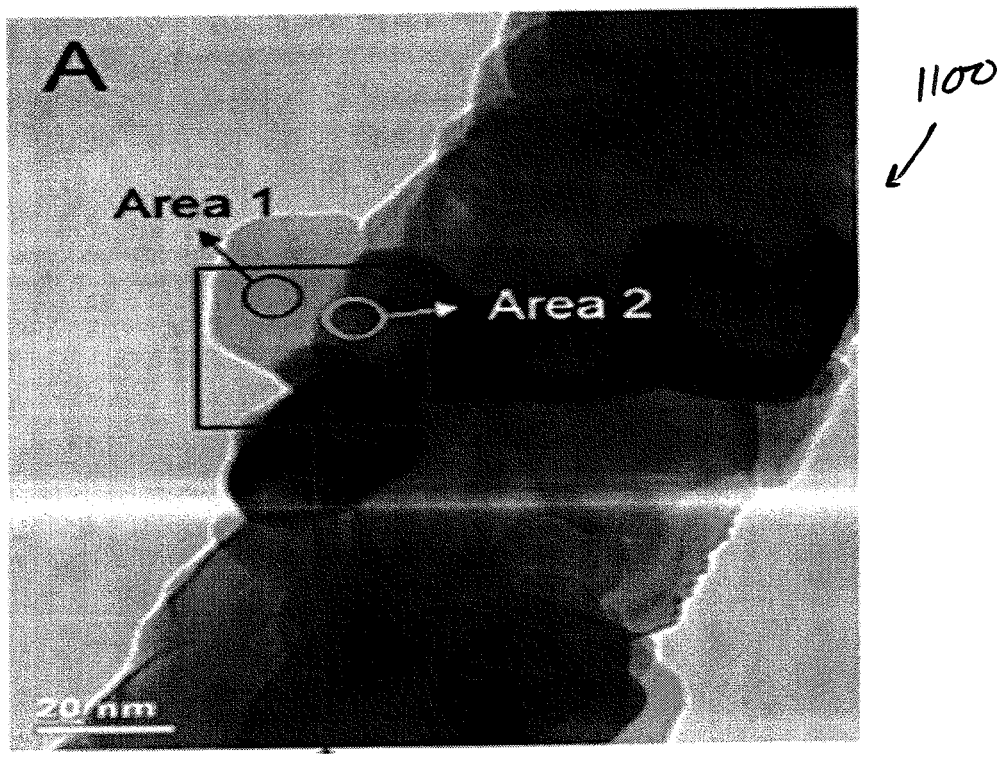
FIG. 11A depicts a high resolution transmission electron microscopy image of a single Ce—Ni—O NF in accordance with exemplary embodiments of the present disclosure.
Figure 11B:
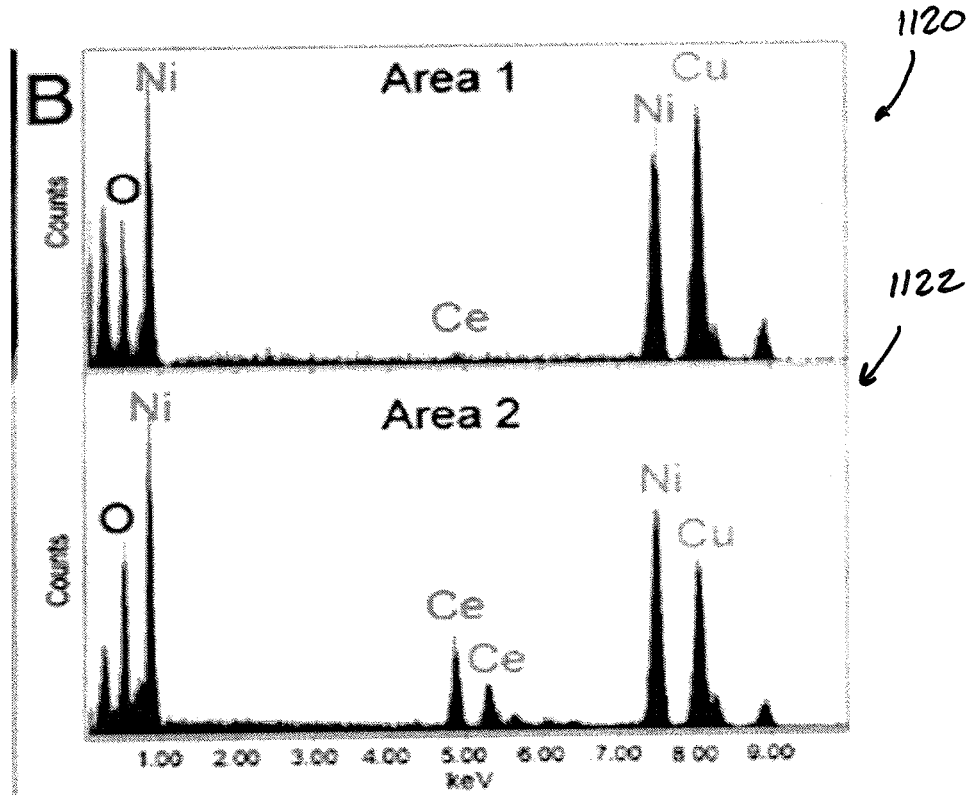
FIG. 11B depicts an energy-dispersive X-ray spectroscopy pattern of small areas on a nanoparticle decorated on a nanofiber surface and on a nanofiber backbone near the surface in accordance with exemplary embodiments of the present disclosure.
Figure 11C:
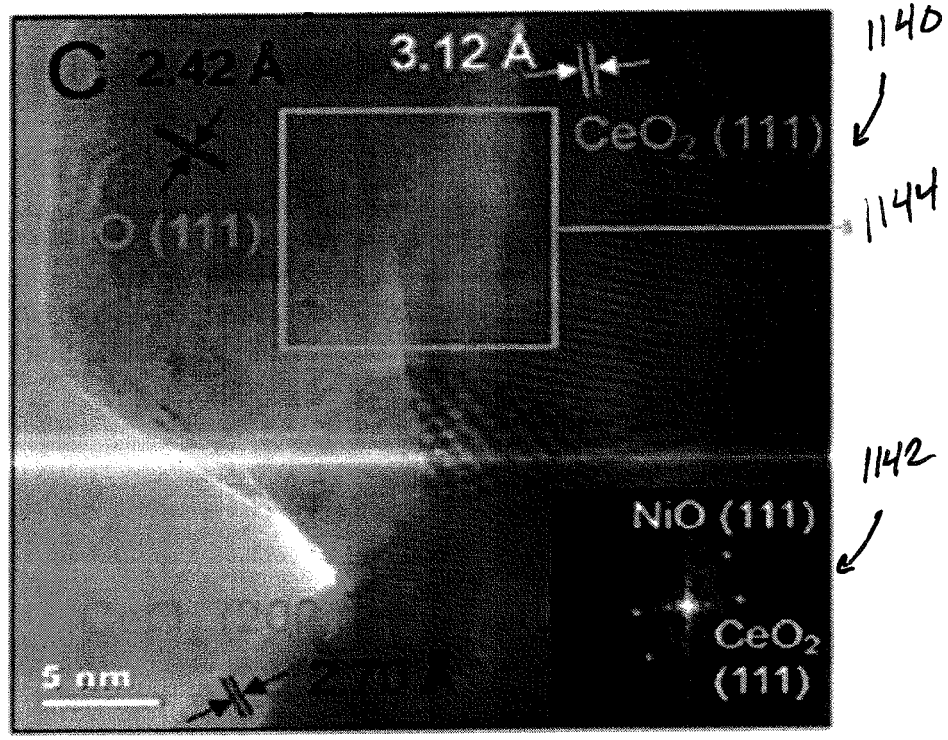
FIG. 11C depicts a high-resolution transmission electron microscopy lattice image of the Ce—Ni—O nanofiber in accordance with exemplary embodiments of the present disclosure.
Figure 11D:
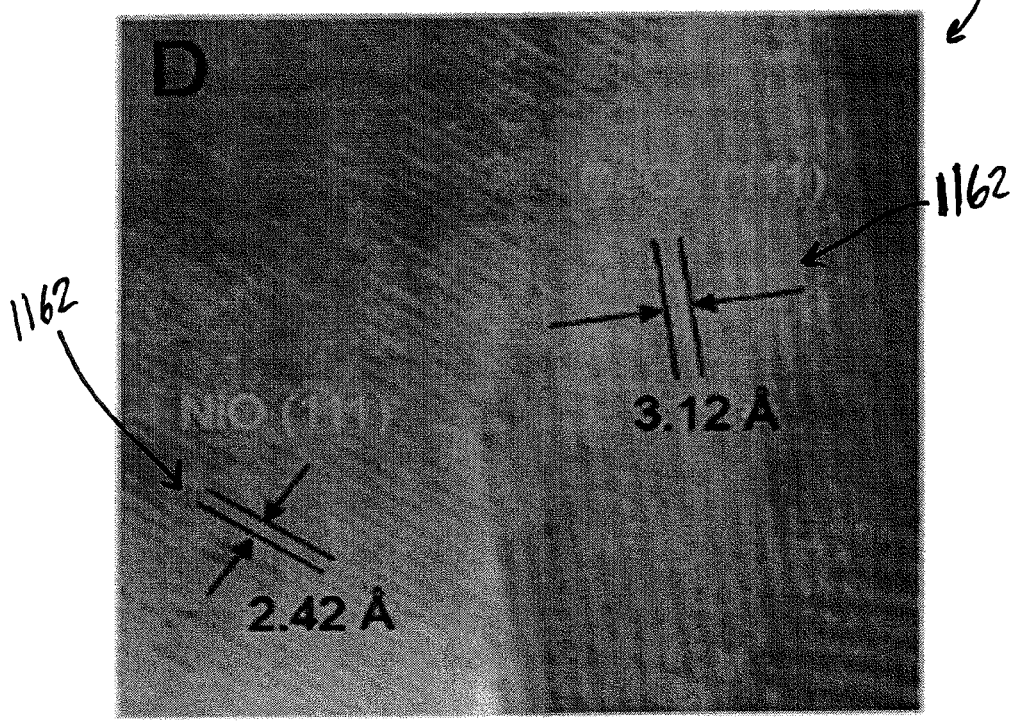
FIG. 11D depicts an enlarged image 1160 of a selected area from FIG. 11C in accordance with exemplary embodiments of the present disclosure.

FIG. 11A depicts a high resolution TEM image 1100 of a single Ce—Ni—O nanofiber 1102. FIG. 11B depicts graphs 120 and 1122 showing an EDX pattern of small areas on a nanoparticle decorated on nanofiber surface and on a nanofiber backbone. FIG. 11C depicts a HRTEM lattice image 1140 of the Ce—Ni—O nanofiber 1102 corresponding to a selected area and shows an FFT image 1142 of the selected area. FIG. 11D depicts an enlarged image 1160 of the selected area from FIG. 11C.

With reference to FIG. 11A, areas 1104 and 1106 are selected on the Ce—Ni—O nanofiber 1102. The areas 1104 and 1106 correspond to the conjunction area of nanofiber backbone and a nanoparticle on the surface. As shown in FIG. 11B, small area EDX spectra of nanoparticle corresponding to the area 1104 in FIG. 11A and of the nanofiber backbone near surface corresponding to the area 1106 indicate the presence of Ni in both areas 1104 and 1106, and the absence of Ce in the nanoparticle, which supports that the nanoparticle on the nanofiber surface is NiO and nanofiber backbone is comprised of both $CeO_2$ and NiO. This is further confirmed by the lattice image. FIGS. 11C and 11D exhibit the combination of crystalline $CeO_2$ and NiO. The crystal structure of crystallite can be identified using fast Fourier transform (FFT) analysis of its lattice image. The FFT image of an edge area 1144 between NiO nanoparticle and nanofiber in FIG. 11C shows two pairs of dots with different distance (inset), indicating the presence of NiO(111) and $CeO_2$(111) crystallites. The same area (the edge area 1144) was further magnified, as presented in FIG. 11D, which clearly shows the interplanar distances 1162 between lattice fringes of 2.42 Å and 3.12 Å, corresponding to NiO (111) on the nanoparticle side and $CeO_2$ (111) on the backbone side, respectively.

It was reported that the Ce—Ni—O oxide composite with high Ni doping have three kinds of co-existed Ni phases: aggregated NiO on the surface of $CeO_2$ support, highly dispersed NiO with strong interaction with $CeO_2$ and Ni atoms incorporated into $CeO_2$ lattice forming $Ce_{1-x}$—$Ni_xO_2$ solid solution. (W. J. Shan, M. F. Luo, P. L. Ying, W. J. Shen, C. Li, Reduction property and catalytic activity of Ce1-XNiXO2 mixed oxide catalysts for CH4 oxidation, *Appl. Catal. A-Gen.*, 246 (2003) 1-9; N. M. Deraz, Effect of NiO content on structural, surface and catalytic characteristics of nanocrystalline NiO/CeO2 system, *Ceram. Int.*, 38 (2012) 747-753). Based on all characterization results of Ce—Ni—O nanofibers above, it can be concluded that (1) Ce—Ni—O nanofibers have closely equal atom ratio of Ce and Ni, (2) highly dispersed NiO, $Ce_{1-x}Ni_xO_2$ solid solution and $CeO_2$ co-exists in the Ce—Ni—O nanofibers backbone with NiO preferentially rich near the surface and (3) aggregated NiO forming nanoparticles on the surface of nanofibers.

Figure 12A:
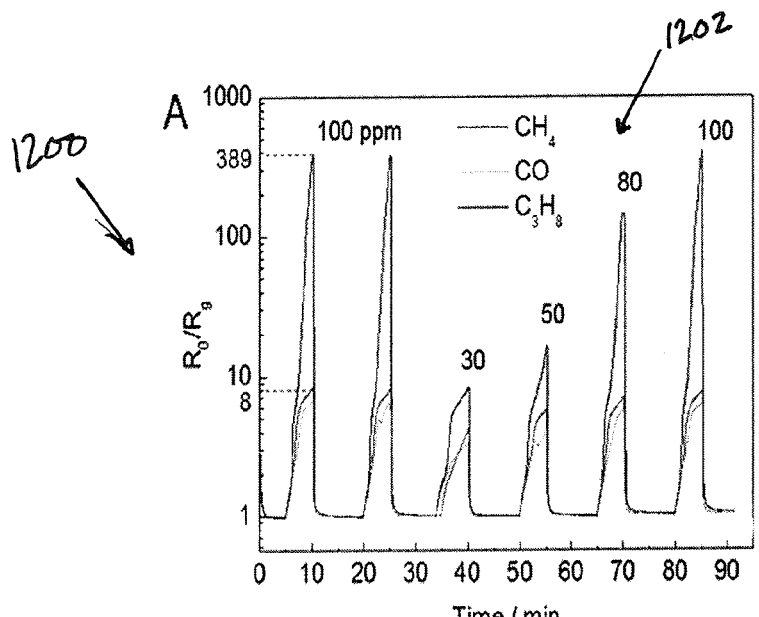
FIG. 12A shows a semi-log plot of real-time sensor responses of Ce—Ni—O nanofibers based sensors upon periodic exposure to different concentrations of CO, $CH_4$ and $C_3H_8$ balanced by $N_2$ at 800° C. with an applied DC bias of 1 V (recovering gas is 1% $O_2/N_2$) in accordance with exemplary embodiments of the present disclosure.
Figure 12B:
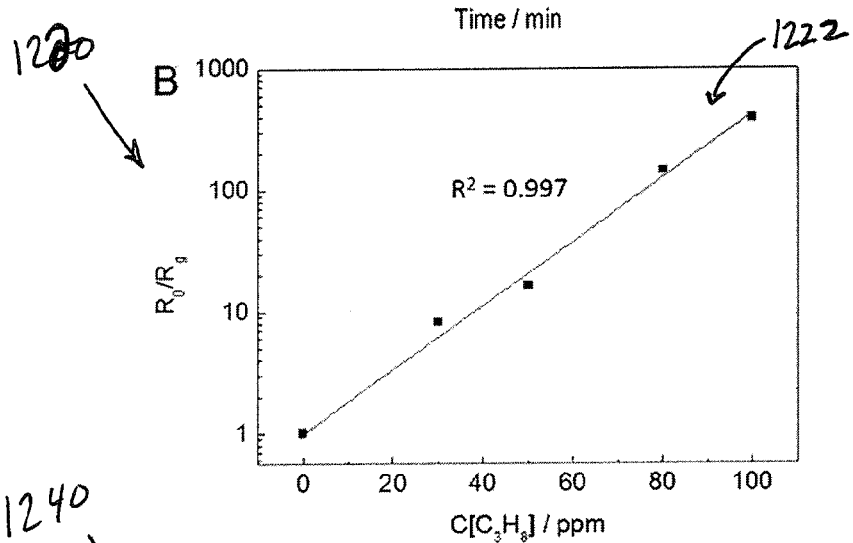
FIG. 12B shows a semi-log plot of calibration curves for $C_3H_8$ in accordance with exemplary embodiments of the present disclosure.
Figure 12C:
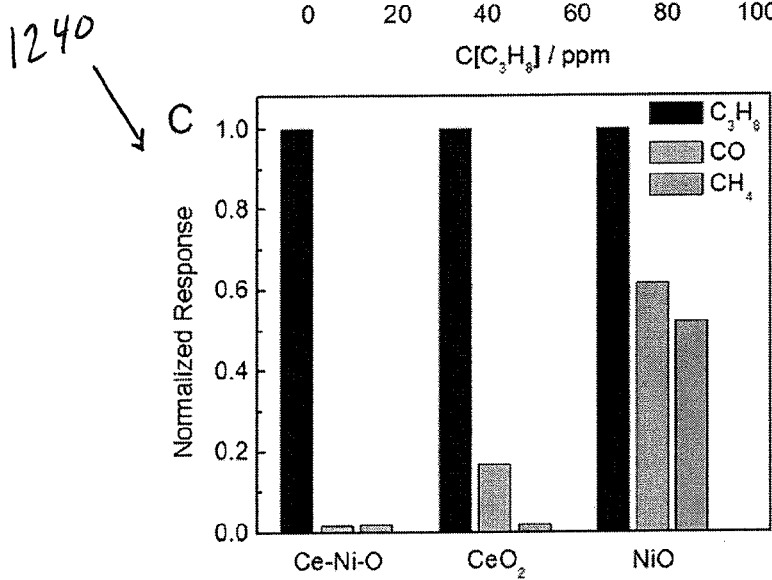
FIG. 12C shows a summarized sensitivity/selectivity of Ce—Ni—O nanofibers, $CeO_2$ nanofibers and NiO nanofibers based gas sensors towards one hundred parts per million reducing gases (CO, $CH_4$ and $C_3H_8$) at 800° C. in accordance with exemplary embodiments of the present disclosure.

The as-prepared Ce—Ni—O nanofibers were employed as the sensing material to detect CO, $CH_4$ and $C_3H_8$ balanced by $N_2$ with different concentrations at 800° C. FIG. 12A depicts a graph 1200 showing a semi-log plot of real-time sensor responses 1202 of Ce—Ni—O nanofiber based sensors upon periodic exposure to different concentrations of CO, $CH_4$ and $C_3H_8$ balanced by $N_2$ at 800° C. with an applied DC bias of 1 V (recovering gas is 1% $O_2/N_2$). FIG. 12B depicts a graph 1220 showing a semi-log plot of calibration curves 1222 for $C_3H_8$. FIG. 12C depicts a graph 1240 that summarizes sensitivity/selectivity of Ce—Ni—O nanofiber, $CeO_2$ nanofiber and NiO nanofiber based gas sensors towards 100 ppm reducing gases (CO, $CH_4$ and $C_3H_8$) at 800° C.

As shown in FIG. 12A, when exposed to reducing gas, the resistance ratio $R_0/R_g$ of the sensor increased (the resistance of the sensor decreased), suggesting n-type sensing behavior. For all test reducing gases, the sensor showed fast response within 5 minutes, rapid recovery by 1% $O_2/N_2$, and concentration-dependent behavior. However, the Ce—Ni—O nanofiber based sensor is selectively ultra-sensitive to propane with the resistance ratio $R_0/R_g$ as high as 389 towards 100 ppm $C_3H_8$ and shows very limited sensitivity to CO and $CH_4$ with the resistance ratio $R_0/R_g$ less than 10. To the same concentration of reducing gas (100 ppm), the sensor showed excellent sensitivity to $C_3H_8$ which is 48-fold and 60-fold higher than the sensitivity to $CH_4$ and CO, respectively. In addition, as shown in FIG. 12B, the calibration curve 1222 for $C_3H_8$ detection in the semi-log plot showed a good liner relation between the sensitivity ($\log(R_0/R_g)$) and the gas concentration within test concentration range. Moreover, good reproducibility of the sensor can be revealed by almost the same response to the same concentration of reducing gas (the first two and last one cycles are in the same concentration). The calculated relative standard deviation (RSD) of sensor responses towards three-time exposure to 100 ppm $C_3H_8$ is 3.3%, indicating the excellent reproducibility to propane detection.

As shown in FIG. 12C, the Ce—Ni—O, $CeO_2$, and NiO nanofiber sensors each had a strong response to propane. However, the response of the Ce—Ni—O nanofiber sensor to CO and $CH_4$ was reduced as compared to the $CeO_2$ and NiO nanofiber sensors. The graph 1240, therefore, illustrate that the Ce—Ni—O nanofiber sensor has a better selectivity than the $CeO_2$ and NiO nanofiber sensors. Particularly, as summarized in FIG. 12C, the Ce—Ni—O nanofiber based sensor showed the best selectivity to $C_3H_8$ over CO and $CH_4$. 100 ppm of CO and $CH_4$ only introduces 1.7% and 2.0% interferences to the response of Ce—Ni—O nanofibers towards the same concentration of $C_3H_8$, respectively. These good sensing results indicate that the Ce—Ni—O nanofibers possesses promising potential as a sensing material for selective propane detection at high temperature.

Figures 13A, 13B:
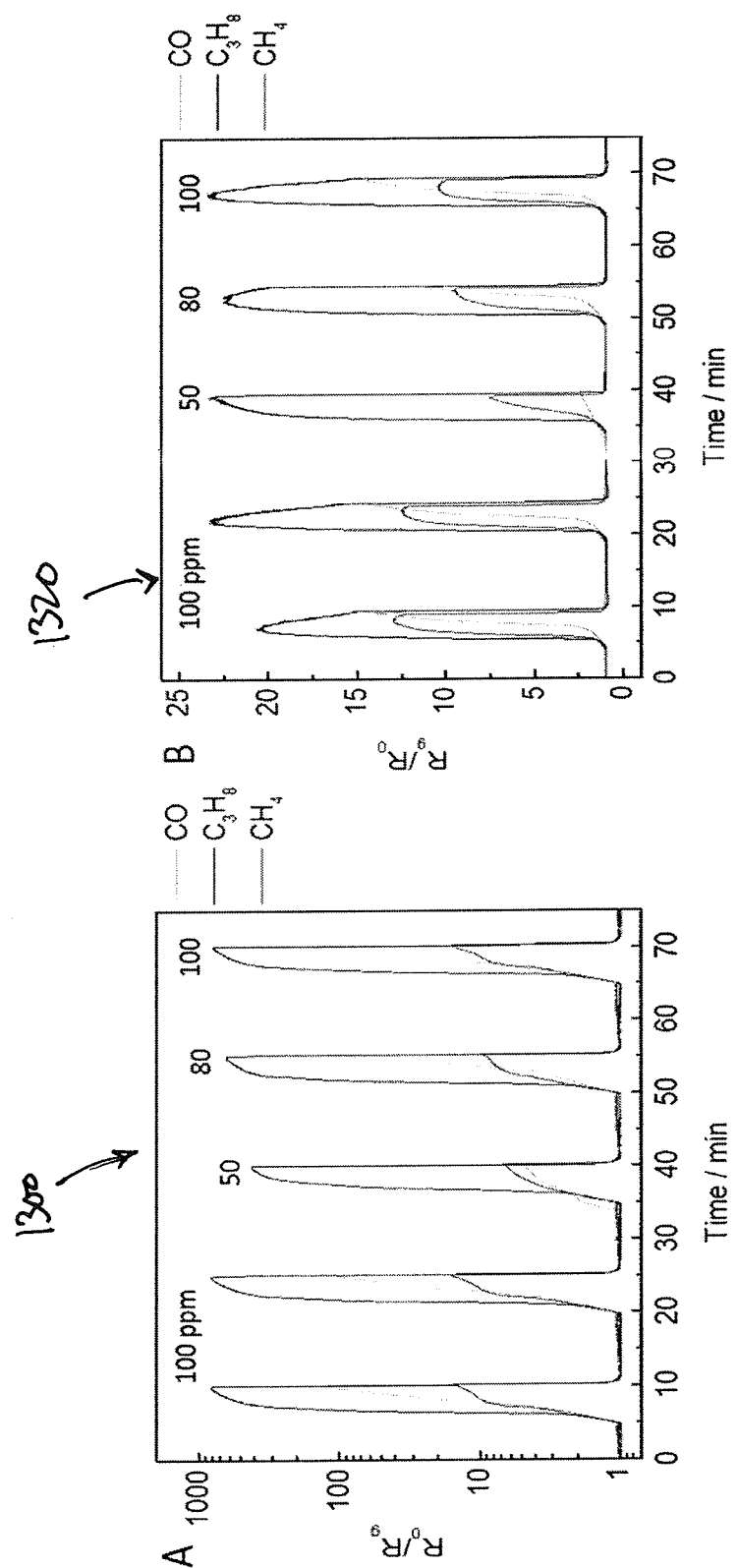
FIG. 13A shows a semi-log plot of real-time sensor responses of $CeO_2$ nanofibers based sensors in accordance with exemplary embodiments of the present disclosure.
FIG. 13B shows a linear plot of real-time sensor responses of NiO nanofibers based sensors upon periodic exposure to different concentrations of CO, $CH_4$ and $C_3H_8$ balanced by $N_2$ at 800° C. with an applied direct current (DC) bias of one volt (recovering gas is 1% $O_2/N_2$) in accordance with exemplary embodiments of the present disclosure.

FIG. 13A depicts a graph 1300 showing a semi-log plot of real-time sensor responses of $CeO_2$ nanofiber based sensors upon periodic exposure to different concentrations of CO, $CH_4$ and $C_3H_8$ balanced by $N_2$ at 800° C. with an applied DC bias of 1 V (recovering gas is 1% $O_2/N_2$). FIG. 13B depicts a graph 1320 showing a linear plot of real-time sensor responses of NiO nanofiber based sensors upon periodic exposure to different concentrations of CO, CH₄ and C₃H₈ balanced by N₂ at 800° C. with an applied DC bias of 1 V (recovering gas is 1% O₂/N₂). CeO₂ nanofiber-based and NiO nanofiber-based sensor were also investigated as control experiments. The sensing performance of CeO₂ nanofiber-based sensor was reported elsewhere. (Y. Liu, X. Sun, B. Li, Y. Lei, Tunable p-n Transition Behaviour of p-La0.67Sr0.33MnO3/n-CeO2 Nanofibers Heterojunction for the Development of Highly Selective High Temperature Propane *Sensor, Journal of Material Chemistry, A*, (2014)). (Results were shown in FIG. 13A). Electrospun NiO nanofibers was fabricated by similar procedure, whose sensing profile under the same test condition was presented in FIG. 13B. CeO₂ nanofiber-based sensor showed ultra-high sensitivity towards propane up to 800 ($R_0/R_g$) after 5 min exposure to 100 ppm C₃H₈. However, the sensor showed saturated pattern for propane concentration dependence and obvious interference from CO. 100 ppm of CO introduces 16.8% interference to the response of CeO₂ nanofibers towards the same concentration of C₃H₈. For NiO nanofiber-based sensor, resistance increased upon exposure to reducing gas (p-type). The sensor exhibited concentration-dependent behavior to both CO and CH₄ from 50 to 100 ppm, however, the sensing response was completely independent with C₃H₈ concentration. In addition, the sensor showed same level responses towards the same concentration (100 ppm) of CO, CH₄ and C₃H₈, resulting in a significant interference with 61.7% from CO and 51.0% from CH₄. To compare the sensing performance among Ce—Ni—O nanofiber, CeO₂ nanofiber and NiO nanofiber-based sensors, normalized response was used to evaluate, using the sensor response ($R_0/R_g$ for Ce—Ni—O nanofibers and CeO₂ nanofibers, $R_g/R_0$ for NiO nanofibers) towards 100 ppm C₃H₈ as the basis of one unit.

The mechanisms of the resistance change of single component CeO₂ and NiO in reducing atmosphere are well-established. CeO₂, with n-type sensing behavior, can be reduced from Ce⁴⁺ to Ce³⁺ with generation of oxygen vacancies and electrons in reducing atmosphere, leading to a resistance decrease following reaction 1:

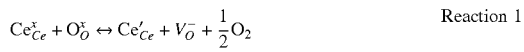

Reaction 1 where $Ce'_{Ce}$ is electron associated with lattice Ce ($Ce_{Ce}^x$), $o_o^x$ and $v_o$ represent lattice oxygen and double ionized oxygen vacancy, respectively. The CeO₂ nanofiber-based sensor showed fast and exceptionally high response towards C₃H₈, indicating the fast reaction kinetics and large extent of electrons produced by extracting lattice oxygen (FIG. 13A).

NiO, as a p-type semiconductor whose intrinsic defects are Ni cation vacancies and holes, can be reduced in reducing atmosphere in following sequence: $Ni^{3+} \rightarrow Ni^{2+} \rightarrow Ni^{\delta+} \rightarrow Ni^0$. $Ni^{3+}$ represents the Ni cation ($Ni^{2+}$) associated with an electron hole due to a nearby Ni cation vacancy. Reduction of NiO from $Ni^{3+}$ to $Ni^{2+}$ decreases the resistance of NiO, which can be expressed as:

Reaction 2 where $v''_{Ni}$ cation vancancy. For NiO nanofiber-based sensor, in the 5 min exposure time to reducing gas, major contributor to the resistance change is the reduction of $Ni^{3+}$ to $Ni^{2+}$. One possible reason for the concentration independent behavior of NiO nanofibers towards C₃H₈ (FIG. 13B) is that the limited concentration of Ni cation vacancies and holes in NiO.

Figures 14A, 14B:
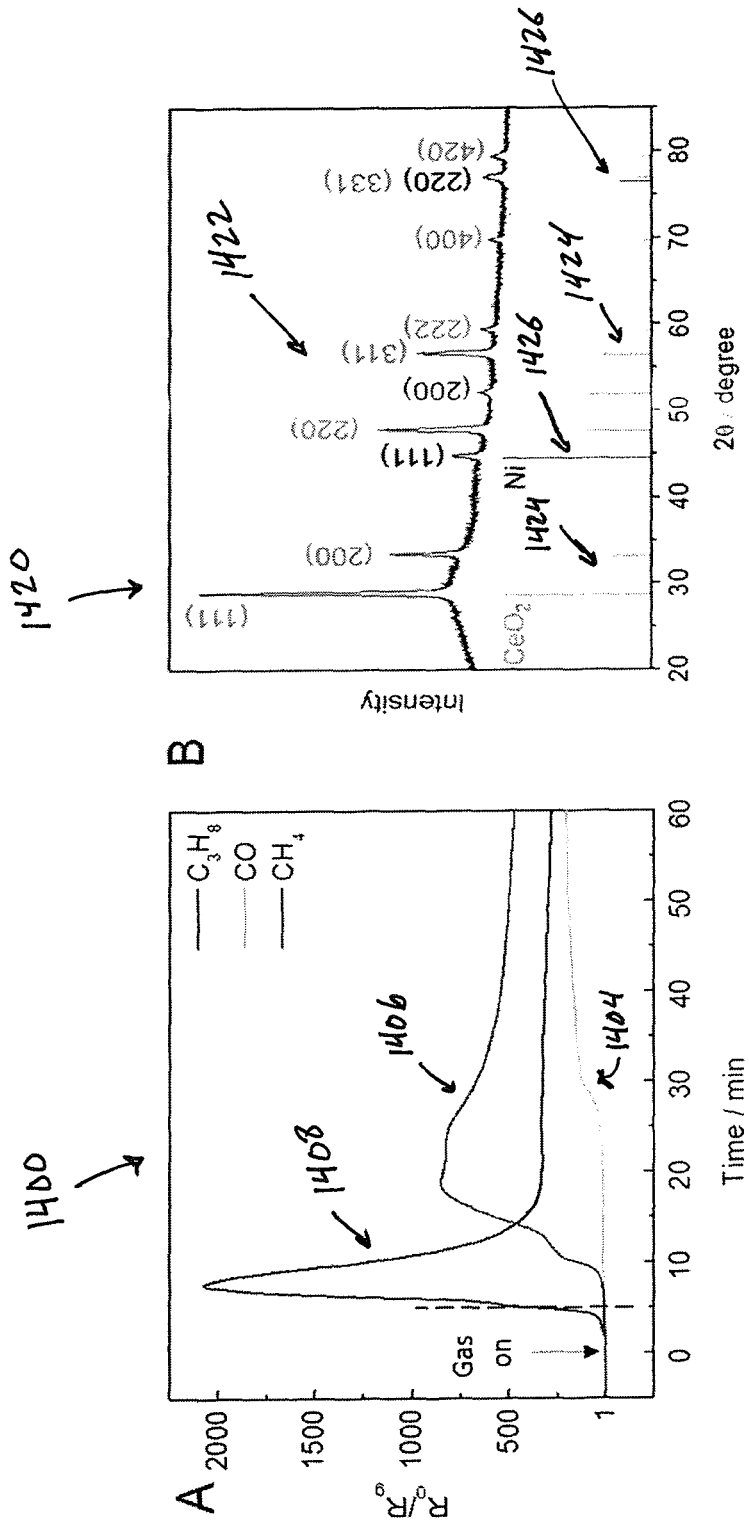
FIG. 14A depicts responses of Ce—Ni—O nanofibers based sensors upon exposure to one hundred parts per million CO, $CH_4$ and $C_3H_8$ balanced by $N_2$ for one hour at an applied direct current (DC) bias of one volt in accordance with exemplary embodiments of the present disclosure.
FIG. 14B depicts X-ray diffraction patterns for reduced Ce—Ni—O nanofibers and standard values for $CeO_2$ and Ni in accordance with exemplary embodiments of the present disclosure.

When combined CeO₂ and NiO in a composite, various defect points and oxygen species co-exist. The sensing mechanism of Ce—Ni—O composite nanofiber-based sensor for the selective propane detection was first investigated by exposing the sensor to 100 ppm reducing gases (CO, CH₄ and C₃H₈) for 1 hour to monitor the resistance change of the sensing material. FIG. 14A shows the real-time resistance change of Ce—Ni—O nanofibers when exposed to reducing gas for 1 h (started from 0 min). The response of the sensor to C₃H₈ is much faster and higher than that to CO or CH₄ in the first 10 minutes, which implies the fast reaction kinetics with C₃H₈. However, after 1-hr exposure of the sensing material to reducing gas, the final resistance change did not show such prominent difference as observed in the first 10 minutes and the sensing material gradually reached the equilibrium in reducing gas. To track the final state of Ce—Ni—O nanofibers after 1 h exposure to reducing gas, the sensor was cooled down to room temperature in reducing atmosphere (e.g. 100 ppm C₃H₈). And the reduced Ce—Ni—O nanofibers was subjected by XRD study to identify the composition change. The XRD pattern of the reduced sensing material was shown in FIG. 14B, which matches the combined standard spectrum of CeO₂ (JCPDS 65-5923) and Ni (JCPDS 04-0850). The formation of metallic Ni is clearly revealed by the diffraction peaks at 2θ values of 44.50, 51.84 and 76.37 corresponding to (111), (200) and (220) crystal planes of Ni, respectively. This result indicates that after long-time exposure to reducing gas, most of NiO has been reduced to metallic Ni while nearly no Ce₂O₃ was detected by XRD, which might be ascribed to oxygen transfer between Ni and Ce to reach the equilibrium, resulting in the formation of metallic Ni and the transition of Ce³⁺ to Ce⁴⁺. Similar phenomena have also been observed in other reports. (W. J. Shan, M. Fleys, F. Lapicque, D. Swierczynski, A. Kiennemann, Y. Simon, P. M. Marquaire, Syngas production from partial oxidation of methane over Ce1-XNiXOY catalysts prepared by complexation-combustion method, *Appl. Catal. A-Gen.*, 311 (2006) 24-33).

Figure 15:
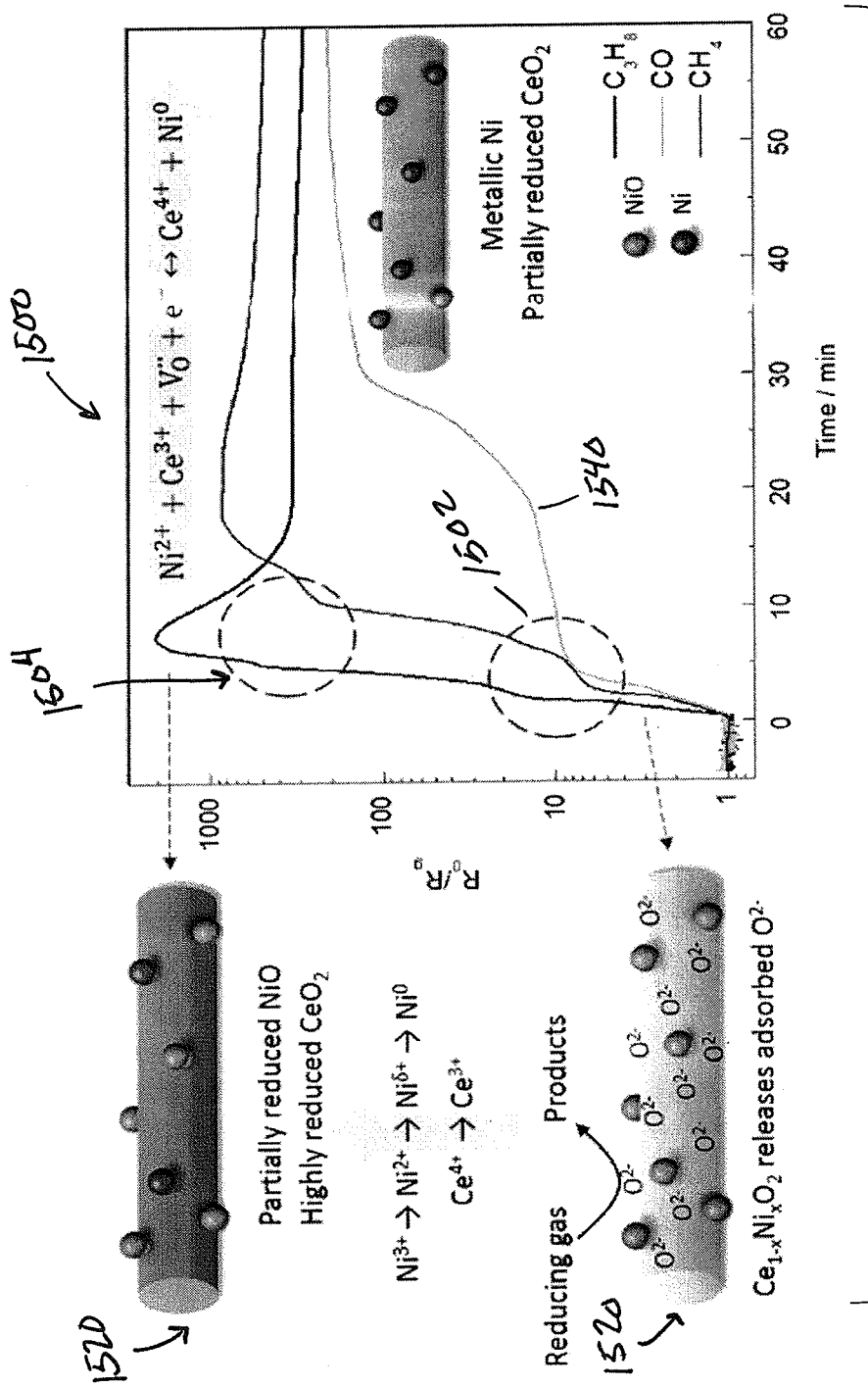
FIG. 15 shows semi-log plot and illustration for proposed sensing mechanism based on observed experimental results for responses of Ce—Ni—O nanofibers based sensors upon exposure to one hundred parts per million CO, $CH_4$ and $C_3H_8$ balanced by $N_2$ for one hour at an applied direct current (DC) bias of one volt in accordance with exemplary embodiments of the present disclosure.

FIG. 14A depicts a graph 1400 showing sensor responses 1402 of Ce—Ni—O nanofiber based sensors upon exposure to 100 ppm CO (denoted by line 1404), CH₄ (denoted by line 1406) and C₃H₈ (denoted by line 1408) balanced by N₂ for one hour at an applied DC bias of 1 V. FIG. 14B depicts a graph 1420 that shows XRD patterns 1422 for the reduced Ce—Ni—O nanofibers and the standard values for CeO₂ (denoted by lines 1424) and Ni (denoted by lines 1426). To better reveal the reaction pattern between sensing material and reducing gas, FIG. 14A was re-plotted using semi-log plot, as shown in FIG. 15 as graph 1500, in which a two-step pattern (denoted by 1502 and 1504) of resistance change upon exposure to 100 ppm CO along with time increase can be seen, presumably indicating two different reactions mechanism or reaction sites associated with Ce—Ni—O nanofibers. Similarly, two small shoulder peaks can also be observed during the exposure to 100 ppm hydrocarbon (CH₄ and C₃H₈) with different increasing rates of sensor response ($R_0/R_g$). Based on previous characterizations, the as-prepared Ce—Ni—O nanofibers 1520 are comprised of highly dispersed NiO, well-distributed CeO₂ and small amount of solid solution Ce₁₋ₓNiₓO in nanofiber backbone, as well as aggregated NiO nanoparticles on the nanofiber surface. Different oxygen species with different reducibility in Ce—Ni—O composites are identified by temperature-programmed reduction (TPR) study and DFT+U calculation. (X. Wang, M. Shen, J. Wang, S. Fabris, Enhanced oxygen buffering by substitutional and interstitial Ni point defects in ceria: A first-principles DFT+U study, *Journal of Physical Chemistry C*, 114 (2010) 10221-10228; S. Xu, X. Yan, X. Wang, Catalytic performances of NiO—CeO2 for the reforming of methane with CO2 and O2, Fuel, 85 (2006) 2243-2247; W. J. Shan, M. F. Luo, P. L. Ying, W. J. Shen, C. Li, Reduction property and catalytic activity of Ce1-XNiXO2 mixed oxide catalysts for CH4 oxidation, *Appl. Catal. A-Gen.*, 246 (2003) 1-9; and N. M. Deraz, Effect of NiO content on structural, surface and catalytic characteristics of nano-crystalline $NiO/CeO_2$ system, Ceram. Int., 38 (2012) 747-753). Thermodynamically, aggregated NiO nanoparticles and highly dispersed NiO in $CeO_2$ can be easily reduced with the relatively high reducibility of the former, while $CeO_2$ possesses a higher reduction temperature. (W. J. Shan, M. F. Luo, P. L. Ying, W. J. Shen, C. Li, Reduction property and catalytic activity of $Ce_{1-x}Ni_xO_2$ mixed oxide catalysts for CH4 oxidation, *Appl. Catal. A-Gen.*, 246 (2003) 1-9). For $Ce_{1-x}Ni_xO_2$ solid solution, $Ni^{2+}$ is incorporated into the lattice of $CeO_2$ to replace some $Ce^{4+}$ cations, in which charge unbalance and lattice distortion happen within the structure of $CeO_2$, leading to the generation of oxygen vacancies. Instead of reduction of Ce ions nor in charge modifications of the $Ni^{2+}$ ions, the O release/uptake in this type of oxygen vacancy determines the appearance/quenching of gap states formed by electron states localized on the O ions neighboring the Ni defect. (X. Wang, M. Shen, J. Wang, S. Fabris, Enhanced oxygen buffering by substitutional and interstitial Ni point defects in ceria: A first-principles DFT+U study, *Journal of Physical Chemistry C*, 114 (2010) 10221-10228). This electronic effect endows $Ce_{1-x}Ni_xO_2$ solid solution with very reactive oxygen species.

Considering the high operation temperature of 800° C., nanoscale sensing material and sensing performance of $CeO_2$ nanofiber and NiO nanofiber based sensors, kinetically, $CeO_2$ can rapidly release and uptake lattice oxygen following reaction 1 and $Ni^{3+}$ can be fast reduced to $Ni^{2+}$ following reaction 2, while further reduction of $Ni^{2+}$ to Ni has a relatively slow kinetics. Therefore, as illustrated in FIG. 15, solid solution $Ce_{1-x}Ni_xO_2$, providing high reactive oxygen species, is ascribed to be responsible for the first step of response towards reducing gas, which can be clearly seen in the CO detection (denoted by line 1540). The reduction of highly reactive oxygen species associated with small amount of $Ce_{1-x}Ni_xO_2$ is rapid by all three reducing gases, which may only increase the response of the sensor by around 10 times according to our experimental data (denoted by line 1502). After these highly reactive oxygen species are completely consumed, reducing gas starts to extract lattice oxygen from $CeO_2$ and NiO. Due to the fast reaction kinetics of $CeO_2$ with $C_3H_8$, the concentration of electrons in Ce—Ni—O nanofibers dramatically increased in the first 7 minutes, along with $Ce^{4+}$ reduced to $Ce^{3+}$ and $Ni^{3+}$ reduced to mainly $Ni^{2+}$ and few $Ni^0$. For propane detection, after $R_0/R_g$ reaches the maximum value, the response of the sensor gradually decreases to an equilibrium state, which can be ascribed to the reaction as follows (W. J. Shan, M. Fleys, F. Lapicque, D. Swierczynski, A. Kiennemann, Y. Simon, P. M. Marquaire, Syngas production from partial oxidation of methane over Ce1-XNiXOY catalysts prepared by complexation-combustion method, *Appl. Catal. A-Gen.*, 311 (2006) 24-33):

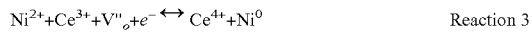

Reaction 3

Oxygen transfer happens between Ni and Ce to reach the equilibrium, resulting in the formation of metallic Ni. Due to different reaction kinetics in lattice oxygen extraction, CO possesses the slowest reaction rate and $CH_4$ shows a moderate reaction rate, meanwhile the oxygen transfer can also occur, leading to a long plateau of sensor response.

In the real-time gas detection experiment, the response time for each sensing cycle upon exposure to reducing gas is set as 5 minutes. In this time range, CO and $CH_4$ just consume the highly reactive oxygen species associated with $Ce_{1-x}Ni_xO_2$ solid solution, giving a relatively low sensitivity (less than 10), while $C_3H_8$ can rapidly extract the lattice oxygen after the consumption of the highly reactive oxygen species in $Ce_{1-x}Ni_xO_2$, resulting in excellent sensitivity and selectivity against CO and $CH_4$ under our tested conditions.

As described herein, the sensing mechanism of Ce—Ni—O nanofibers for the selective propane detection is proposed by considering several potential contributors. On one hand, multiple-step reaction mechanism and varied kinetic rates for different reducing gas play a significant role in the excellent sensitivity and selectivity of propane detection against CO and $CH_4$. On the other hand, the trade-off effect between n-$CeO_2$ and p-NiO also plays a role in the observed response. The sensing response of Ce—Ni—O nanofibers shows n-type behavior (FIG. 12A), indicating that the response of the Ce—Ni—O nanofibers composite was dominated by $CeO_2$. Individually, $CeO_2$ and NiO show responses towards reducing gas in an opposite direction, which results in overall reduced sensitivity of Ce—Ni—O nanofibers compared to $CeO_2$ nanofibers due to the trade-off effect. However, because of the different extent of such offset effect contributed by NiO towards different reducing gases, the sensitivity towards CO, $CH_4$ and $C_3H_8$ varied greatly. For CO and $CH_4$, both $CeO_2$ and NiO shows concentration-dependent behavior in opposite direction (FIGS. 13A and 13B), which means the offset extent in Ce—Ni—O nanofibers is proportional to concentration, resulting in a saturation pattern of their sensing behaviors. However, due to the concentration independence of NiO towards propane, the offset extent is fixed despite of propane concentration change. Therefore, a liner relation between sensor response $\log(R_0/R_g)$ and gas concentration was obtained.

As described herein, exemplary embodiments of the present disclosure provide for electrospun Ce—Ni—O composite nanofibers to be employed in sensors to detect reducing gas (CO, $CH_4$ and $C_3H_8$) at high temperature of 800° C. Exemplary embodiments of the electrospun Ce—Ni—O composite nanofibers based sensors shows an excellent sensitivity and selectivity towards $C_3H_8$. Upon the exposure to reducing gas, highly reactive oxygen species associated with solid solution $Ce_{1-x}Ni_xO_2$ are firstly consumed, followed by extraction of lattice oxygen in $CeO_2$ and NiO. Due to the different reduction kinetic rates in the first 5 minute (time scale set for sensing), propane can rapidly consume highly reactive oxygen species associated with solid solution $Ce_{1-x}Ni_xO_2$ and then extract lattice oxygen, leading to significant change of resistance of Ce—Ni—O nanofibers composite, while CO and $CH_4$ possess the sluggish to moderate reduction kinetics, thus only consuming all highly reactive oxygen species. The observed good sensitivity and selectivity can be attributed to such kinetics difference. In addition, the responses of n-$CeO_2$ and p-NiO in Ce—Ni—O nanofibers composites towards reducing gas are in opposite direction. Although the offset effect results in an overall reduced sensitivity, the concentration independence of NiO to $C_3H_8$ further improves the selectivity of the Ce—Ni—O nanofiber based sensor. These results indicate that Ce—Ni—O nanofibers is a promising material in the development of high temperature gas sensor for selective propane detection.

III. Exemplary Gas Sensors

Figure 16:
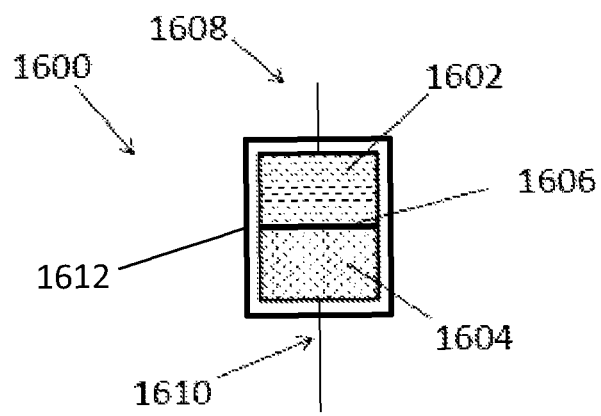
FIG. 16 is a schematic diagram of an exemplary gas sensor formed in accordance with exemplary embodiments of the present disclosure.
Figure 17:
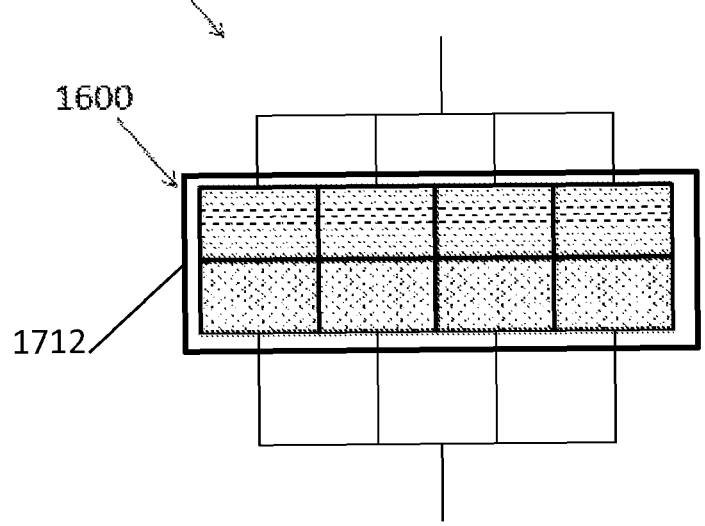
FIG. 17 is a schematic diagram of an exemplary gas sensor array formed in accordance with exemplary embodiments of the present disclosure.

FIG. 16 is a schematic diagram illustrating an exemplary gas sensor 1600 that can be formed in accordance with exemplary embodiments of the present disclosure. In exemplary embodiments, the gas sensor can be used in automotive or power industry applications characterized by emission of carbon monoxide and/or hydrocarbon gas. The gas sensor 1600 includes one or more p-type and n-type nanofiber materials 1602 and 1604, respectively, that form composite nanofibers described herein. The nanofiber composite can be disposed on a substrate 1612 as described herein, and the composite nanofibers can form p-n hetrojunctions 1606 that are responsive to reducing gases (e.g., CO, $CH_4$ and $C_3H_8$) at high temperatures (e.g., 600-1200° C.). Electrodes 1608 and 1610 disposed on the substrate are operative coupled to the nanofibers. As one example, the gas sensor 1600 can be formed by electrospun LSMO-$CeO_2$ nanofiber composites, where the LSMO forms the p-type nanofiber material 1602, $CeO_2$ forms the n-type nanofiber material 1604 and junction between the LSMO and the $CeO_2$ forms the p-n junction 1606. FIG. 17 is a schematic diagram illustrating an exemplary gas sensor array 1700 that can be formed by a plurality of gas sensors 1600 with a single substrate 1712 (or with multiple substrates) in accordance with exemplary embodiments of the present disclosure.

Figure 18:
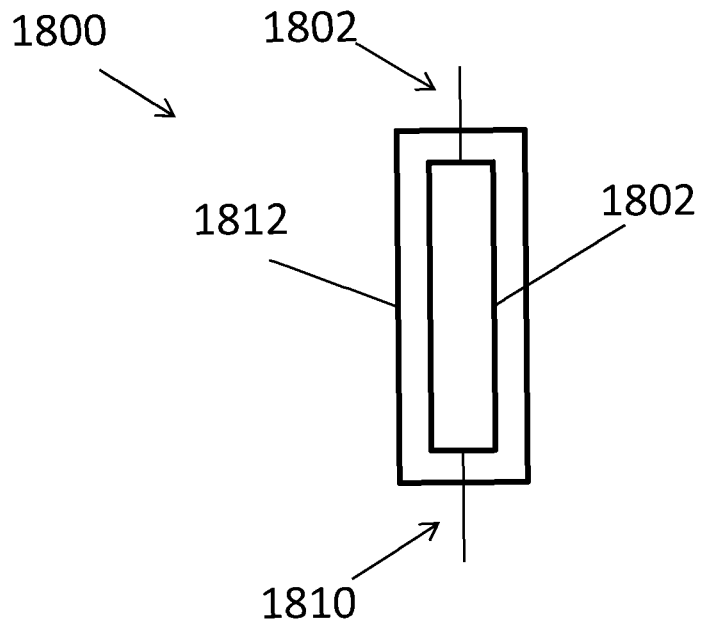
FIG. 18 is a schematic diagram of an exemplary gas sensor formed in accordance with exemplary embodiments of the present disclosure.
Figure 19:
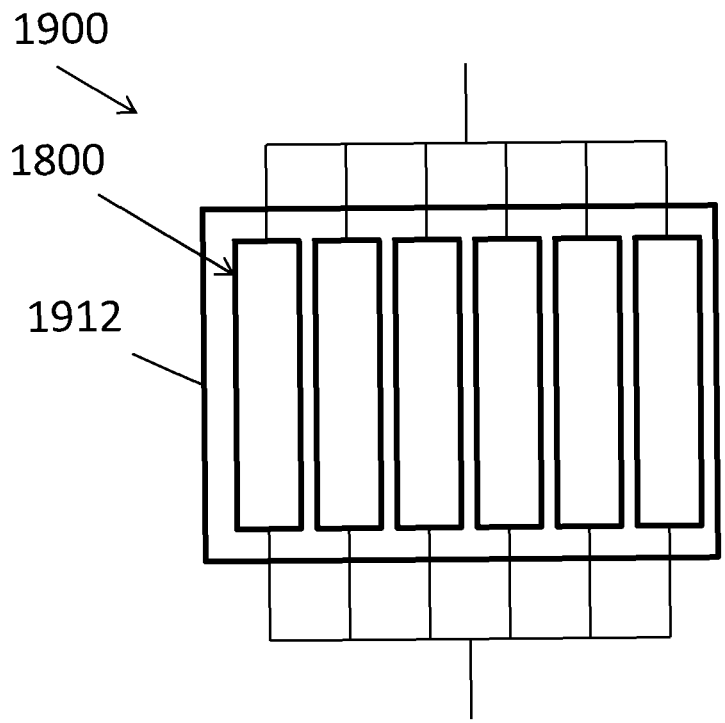
FIG. 19 is a schematic diagram of an exemplary gas sensor array formed in accordance with exemplary embodiments of the present disclosure.

FIG. 18 is a schematic diagram illustrating an exemplary gas sensor 1800 that can be formed in accordance with exemplary embodiments of the present disclosure. In exemplary embodiments, the gas sensor 1800 can be used in automotive or power industry applications characterized by emission of carbon monoxide and/or hydrocarbon gas. The gas sensor 1800 includes one or more p-type and n-type nanofiber materials that form composite nanofibers described herein. The nanofiber composite can be disposed on a substrate 1812 as described herein, and the composite nanofibers can form a resistive element 1802 that is responsive to reducing gases (e.g., CO, $CH_4$ and $C_3H_8$) at high temperatures (e.g., 600-1200° C.). Electrodes 1808 and 1810 disposed on the substrate are operative coupled to the nanofiber composite. As one example, as described herein the gas sensor 1800 can be formed from electrospun Ce—Ni—O composite nanofibers to detect reducing gases, where the NiO forms the p-type nanofiber material, $CeO_2$ forms the n-type nanofiber material, and the nanofiber composite formed by the NiO and $CeO_2$ create the resistive element 1802. FIG. 19 is a schematic diagram illustrating an exemplary gas sensor array 1900 that can be formed by a plurality of gas sensors 1800 in accordance with exemplary embodiments of the present disclosure.

Exemplary embodiments of the gas sensors disclosed herein (e.g., gas sensors formed with Ce—Ni—O composite nanofibers and gas sensors with LSMO-$CeO_2$ nanofiber composite) show good sensitivity, full recovery, fast response and excellent reproducibility. Also disclosed herein are various approaches to improve the selectivity of such high temperature gas sensors, including impedancemetric technique and p-n junction based gas sensors. As described herein, electrospun metal oxide nanofibers provide for nanomaterials employed for gas detection in harsh environment.

All documents cited herein are expressly incorporated by reference herein in their entirety and for all purposes.

While exemplary embodiments of the present disclosure have been described herein, it will be understood by those skilled in the art that various changes may be made and equivalents may be substituted for the elements thereof without departing from the scope of the invention. In addition, many modifications may be made to adapt the teaching of the invention to particular use, application, manufacturing conditions, use conditions, composition, medium, size, and/or materials without departing from the essential scope and spirit of the invention. Therefore, it is intended that the invention not be limited to the particular embodiments and best mode contemplated for carrying out this invention as described herein.

The invention claimed is:

1. A sensor comprising:
a substrate;
one or more electrodes disposed on the substrate; and
an electro spun nanofiber composite formed of a p-type nanofiber material and an n-type nanofiber material,
wherein the nanofiber composite formed by the p-type nanofiber material and the n-type nanofiber material have selectivity towards detecting a specified type of gas,
wherein the nanofiber composite is formed from Lanthanum Strontium Manganate Oxide (LSMO) nanofibers and Cerium (IV) Oxide ($CeO_2$) nanofibers.

2. The sensor of claim 1, wherein the nanofiber composite has a selectivity towards reducing gases including at least one of carbon monoxide, methane and propane.

3. The sensor of claim 1, wherein the p-type material and the n-type material form one or more p-n junctions.

4. The sensor of claim 1, wherein the LMSO nanofibers are $La_{0.67}Sr_{0.33}MnO_3$ nanofibers fabricated by a facile two-step synthetic process that includes electrospinning followed by calcination.

5. The sensor of claim 1, wherein the $CeO_2$ nanofibers are fabricated by a facile two-step synthetic process that includes electrospinning followed by calcination.

6. The sensor of claim 1, wherein the nanofiber composite has a weight ratio of approximately eighty percent $CeO_2$ and approximately twenty percent LSMO.

7. The sensor of claim 1, wherein the nanofiber composite has a weight ratio of $CeO_2$ prepared by sonication that is at least one of twenty-five percent, fifty percent, seventy percent, seventy-five percent, eight percent, or ninety percent.

8. The sensor of claim 1, wherein the sensor comprises an array of gas sensors including a plurality of nanofiber composites including a first nanofiber composite that has a weight ratio of approximately seventy percent $CeO_2$ and approximately thirty percent LSMO and a second nanofiber composite that has a weight ratio of eighty percent $CeO_2$ and approximately twenty percent LSMO, the first nanofiber composite being operable to distinguish carbon monoxide and propane by opposite response directions, and the second nanofiber composite having a sensitivity and selectivity for propane.

9. The gas sensor of claim 1, wherein the nanofiber composite is formed by a metal oxide and Cerium (IV) Oxide ($CeO_2$).

10. The gas sensor of claim 7, wherein the metal oxide is Nickel Oxide (NiO).

11. The gas sensor of claim 1, wherein the nanofiber composite has a sensitivity and selectivity for propane.

12. The gas sensor of claim 1, wherein the gas detected by the p-n junction corresponds to at least one of carbon monoxide or hydrocarbon gas emitted in an automotive or power industry application.

13. A nanofiber composite have a sensitivity and selectivity for detecting a reducing gas, the nanofiber composite comprising:
a plurality of Lanthanum Strontium Manganate Oxide (LSMO) nanofibers;

a plurality of Cerium (IV) Oxide ($CeO_2$) nanofibers,
wherein the LMSO nanofibers and the $CeO_2$ nanofibers are mixed to have a specified weight ratio for sensitivity and selectivity towards a reducing gas.

14. The nanofiber composite of claim 13, wherein the nanofiber composite has a weight ratio of approximately eighty percent $CeO_2$ and approximately twenty percent LSMO.

15. The nanofiber composite of claim 13, wherein the nanofiber composite has a weight ratio of $CeO_2$ prepared by sonication that is at least one of twenty-five percent, fifty percent, seventy percent, seventy-five percent, eight percent, or ninety percent.

16. A composite nanofiber having a sensitivity and selectivity for detecting a reducing gas, the composite nanofiber comprising:
Nickel Oxide (NiO), Cerium (IV) Oxide ($CeO_2$), and a solid solution of $Ce_{1-x}Ni_xO_2$ within a single nanofiber,
wherein nanoparticles of Nickel Oxide (NiO) on a surface of the nanofiber composite comprises a backbone of the Cerium (IV) Oxide ($CeO_2$) and the solid solution of $Ce_{1-x}Ni_xO_2$.

17. A sensor comprising:
a substrate;
two or more electrodes disposed on the substrate; and
at least one composite nanofiber having a backbone formed of a p-type oxide material and an n-type oxide material,
wherein the p-type oxide material and the n-type oxide material of the composite nanofiber are distributed throughout the backbone.

18. The sensor of claim 17, wherein composite nanofiber is a Ce—Ni—O which includes p-type Nickel Oxide (NiO), n-type Cerium (IV) Oxide ($CeO_2$), and solid solution of $Ce_{1-x}Ni_xO_2$ within a single nanfiber.

19. The sensor of claim 18, wherein the composite nanofiber is fabricated by a facile two-step synthetic process that includes electrospinning followed by calcination.

20. A sensor comprising:
a substrate;
two or more electrodes disposed on the substrate; and
an electro spun nanofibers composite that is a physical mixture of the p-type nanofiber material and the n-type nanofiber material,
wherein the p-type nanofiber material is Lanthanum Strontium Manganate Oxide (LSMO) nanofibers and the n-type material is Cerium (IV) Oxide ($CeO_2$) nanofibers.

21. The sensor of claim 20, wherein the physical mixture is achieved via sonication.

22. The sensor of claim 20, wherein the p-type material and the n-type material in the nanofibers composite form a plurality of p-n junctions form a plurality of p-n junctions.

23. The sensor of claim 17, where the backbone is formed of Cerium (IV) Oxide ($CeO_2$) and a solid solution of $Ce_{1-x}Ni_xO_2$.

* * * * *